United States Patent [19]
Proctor et al.

[11] Patent Number: 6,130,228
[45] Date of Patent: Oct. 10, 2000

[54] POLYCYCLIC COMPOUNDS

[75] Inventors: George Rennet Proctor, Stirling; Alan Lang Harvey, Glasgow; Maureen Theresa McKenna, Denny; Steven John Mullins, Esh Winning, all of United Kingdom

[73] Assignee: University of Strathclyde, Glasgow, United Kingdom

[21] Appl. No.: 09/077,453

[22] PCT Filed: Nov. 28, 1996

[86] PCT No.: PCT/GB96/02945

§ 371 Date: Aug. 25, 1998

§ 102(e) Date: Aug. 25, 1998

[87] PCT Pub. No.: WO97/19929

PCT Pub. Date: Jun. 5, 1997

[30] Foreign Application Priority Data

Nov. 29, 1995 [GB] United Kingdom .................. 9524346

[51] Int. Cl.$^7$ ...................... A61K 31/473; C07D 221/18; C07D 221/08
[52] U.S. Cl. ........................ 514/284; 514/290; 514/297; 546/61; 546/79; 546/93; 546/102; 546/104; 546/105
[58] Field of Search ................... 546/61, 79, 93, 546/102, 104, 105; 514/290, 297, 284

[56] References Cited

U.S. PATENT DOCUMENTS 3,232,945  2/1966  Sigale, Jr. et al. .

FOREIGN PATENT DOCUMENTS

| 0 268 871 | 6/1988 | European Pat. Off. . |
| 0 282 959 | 9/1988 | European Pat. Off. . |
| 0 311 303 | 4/1989 | European Pat. Off. . |
| 0 595 365 | 5/1994 | European Pat. Off. . |
| 532 397 | 8/1931 | Germany . |

OTHER PUBLICATIONS

Shri Nivas rastogi, Indian Journal of Pharmacology, pp. 44–48, Nov. 4, 1986.

Acta Chemica Scandinavica, vol. b–33, No. 5, 1979, "Phosphoramides.X.Phosphorus Pentaoxide Amine Mixtures and HMPT as Reagents in the Synthesis of 4–Amino– and 4–dimethylamino–2,3–polymethylenequinolnes", pp. 313–318, Arne Osbirk et al.

Journal Of The Chemical Society, 1947, Letchworth GB, "Some amino–derivatives of dihydro–beta–quinindenes and tetrahydroacridine", pp. 634–637, V. Petrow.

Collection of Czechoslovak Chemical Communications, vol. 42, No. 9, 1977, "Analogues of 9–amino–1,2,3,4–tetrahydroacridine", pp. 2802–2808, J. Bielavsky.

Chemical Abstract No. 43073F—vol. 89, No. 5, Jul. 31, 1978, Joshi Krishna et al, "Possible Psychopharmacological Agents", p. 599.

Chemical Abstract No. 120411d—vol. 81, No. 19, Nov. 11, 1974, M.E. Konshin et al, "2,3–Polymethylenequinolines", p. 515.

Chemical Abstract No. 42310n—vol. 79, No. 7, Aug. 20, 1973, M.E. Konshin, "2,3–Polymethylenequinolines", p. 343.

Chemical Abstract No. 42311p—vol. 79, No. 7, Aug. 20, 1973, M.E. Konshin et al, "2,3–Polymethylenequinolines", p. 343.

Chemical Abstract No. 112191u—vol. 108, No. 13, Mar. 28, 1988, Jasjit S. Bindra et al, "Synthesis, pharmacological activities and physicochemical properties of 4–(substituted amino/N4–arylpiperaziny/aminocarbonyl)–2,3–polymethylenequinolines", p. 604.

Chemical Abstract No. 196226c—vol. 106, No. 23, Jun. 8, 1987, Mohan Prasad et al, "Synthesis and antiarrhythnic activity of 4–substituted 2,3–(tetra/penta/hexamethylene-) quinolines", p. 724.

Chemical Abstract No. 53475t, vol. 74, No. 11, Mar. 15, 1971, M.E. Konshin et al, "Heterocyclic compounds", p. 335.

Chemical Abstract No. 77027d, vol. 73, No. 15, Oct. 12, 1970, E.S. Abramochkin et al, "Synthesis of N–substituted 4–amino–2,3–pentamethylenequinolines", p. 350.

*Primary Examiner*—Alan L. Rotman
*Assistant Examiner*—Rita Desai
*Attorney, Agent, or Firm*—Alston & Bird LLP

[57] ABSTRACT

Compounds of Formula (I), methods for their preparation, pharmaceutical formulations and use thereof.

(I)

10 Claims, No Drawings

POLYCYCLIC COMPOUNDS

This application is a 371 of PCT/GB96/02945 filed Nov. 28, 1996.

BACKGROUND

The present invention relates to compounds which have been found to exhibit anti-acetylcholinesterase activity and/or inhibition of 5-HT uptake and/or inhibition of noradrenaline uptake. More specifically, the invention concerns polycyclic compounds and analogues thereof, methods for their preparation, pharmaceutical formulations containing them and their use as neurotransmitter potentiating agents, in particular in the treatment of symptoms of Alzheimer's disease.

Much work has been done in research in the area of drugs affecting neurotransmitter systems in the central nervous system (CNS). Neurotransmitter molecules are involved in rapid communication in the normal CNS and in pathologic conditions of the CNS. Most of the drugs available to the psychiatrist or neurologist for the treatment of CNS disease function by affecting neurotransmitter pathways directly or indirectly. Of all the CNS disorders known to date, those associated with organic or degenerative dementia are not able to be treated effectively with the range of drugs currently available. A particular disorder, Alzheimer's disease, also known as degenerative dementia, senile dementia, senile dementia of the Alzheimer type and organic brain syndrome, has no known effective treatment therefor.

Certain drugs, such as so-called centrally active muscarinic drugs (i.e. drugs which act directly on the acetylcholine receptors to produce a response), act on so-called muscarinic receptors. Muscarinic receptors have been found to be made up of at least 3 subclasses: $M_1$, $M_2$ and $M_3$. These receptors are found in the brain, heart and gut, and as a result, the use of muscarinic drugs carries with it the possibility of undesirable side effects such as nausea or slowing or stopping of the heart.

Tacrine, a tricyclic acetylcholine esterase inhibitor is known to produce liver damage as a side effect, which, although not believed to be irreversible in nature, is nevertheless undesirable.

There exists a need to provide more effective drugs for the treatment of, or alleviation of symptoms of organic or degenerative dementia diseases of the CNS.

SUMMARY OF INVENTION

It is an object of the invention to provide more effective and/or selective polycyclic drugs for the treatment of, or alleviation of symptoms of organic or degenerative dementia diseases of the CNS.

This and other objects of the invention will become apparent from the following description and examples.

STATEMENT OF INVENTION

According to the present invention there is provided compounds of general Formula (I):

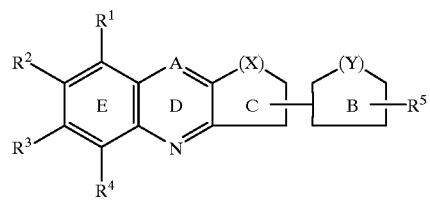

wherein
$R^1$ is selected from $NH_2$, OH, H, F, Cl, Br, I, $OCH_3$, $C_1$–$C_6$ alkyl or aryl (phenyl);
$R^2$ is selected from H, Cl, Br, F, I, OH, $C_1$–$C_6$ alkyl or $C_1$–$C_6$ alkoxy;
$R^3$ is selected from H, F, Cl, Br, I, OH, $OCH_3$ or $C_1$–$C_6$ alkyl;
$R^4$ is selected from H, F, Cl, Br, I, OH, $OCH_3$ or $C_1$–$C_6$ alkyl;
$R^5$ is selected from H, Br, F, Cl, I, NO, $NR^6R^7$, $(CH_2)_{1-4}NR^6R^7$, OH, $C_1$–$C_4$ alkyl and $C_1$–$C_4$ alkoxy;
$R^6$ is selected from H and $C_1$–$C_4$ alkyl;
$R^7$ is selected from H and $C_1$–$C_4$ alkyl;
X represents $(CH_2)$, wherein n is a whole integer selected from 1, 2, 3 or 4;
Y represents $(CH)_m$ or $(CH_2)_m$ wherein m is a whole integer selected from 1, 2, or 3;
A represents C— $NHR^9$ wherein $R^9$ is selected from H, $C_1$–$C_6$ alkyl or aryl;
Ring B is a saturated or unsaturated carbon membered ring optionally fused to Ring C at any face of Ring C which does not extend from a carbon of Ring D such that when Ring B is fused to Ring C, Ring C is optionally substituted at unfused carbon atoms by one or more groups independently selected from H, $C_1$–$C_6$ alkyl or —$COOR^8$ wherein $R^8$ is selected from H or $C_1$–$C_6$ alkyl with the proviso that when Ring C is a 5 or 6 carbon membered ring and is not fused to a ring B at least one of $R^1$, $R^2$, $R^3$ and $R^4$ is not H.

Generic Formula (I) can be viewed as two further subgeneric Formulae (II) and (III). Formula (II) may be viewed as:

(II)

wherein
$R^5$ is selected from H, F, Br, Cl, $NO_2$, $NR^6R^7$, $(CH_2)_{1-4}NR^6R^7$, OH, $C_1$–$C_4$ alkyl and $C_1$–$C_4$ alkoxy;
$R^6$ is selected from H and $C_1$–$C_4$ alkyl;
$R^7$ is selected from H and $C_1$–$C_4$ alkyl;
$R^1$, $R^2$, $R^3$ and $R^4$ are independently selected from H, F, Cl and $OCH_3$;
Ring B can be fused with any face of Ring C which does not extend from a carbon of Ring D;
Ring C is optionally substituted at unfused carbon atoms by one or more groups independently selected from $C_1$–$C_6$ alkyl or $COOR^8$ wherein $R^8$ is H or $C_1$–$C_6$ alkyl; and
X is $(CH_2)$, wherein n is a whole integer selected from 1, 2 or 3.

Naturally the skilled addressee will appreciate that free acid addition salts of compounds of Formula (I) and Formula (II) are encompassed within the present invention.

Suitable acid addition salts include those formed from hydrochloric, hydrobromic, nitric, perchloric, sulphuric, citric, tartaric, phosphoric, lactic, benzoic, glutamic, oxalic, aspartic, pyruvic, succinic, fumaric, maleic, oxaloacetic, isethionic, stearic, phthalic, methanesulphonic, p-toluene sulphonic, benzenesulphonic, lactobionic and glucuronic acids. Most preferably, the salts will be pharmaceutically acceptable.

Compounds of Formula (II) can also be viewed as subgeneric formulae (II(a))

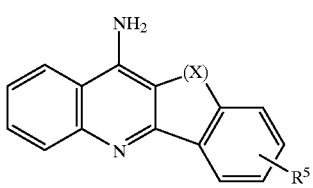
(II(a))

and (II(b))

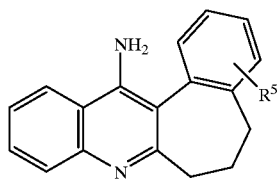
(II(b))

wherein $R^5$ and X are as defined for Formula (II), above.

Unless otherwise indicated, alkyl groups of $R^6$, $R^7$ and $R^8$ in Formulae (I) and (II), may be straight or branched chain alkyl groups such as isopropyl, propyl, butyl, isobutyl, tertbutyl and the like.

Preferred compounds according to subgeneric Formula (II) on the basis of their activity include:

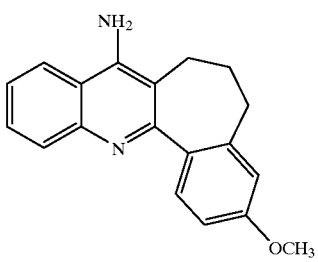
(1)

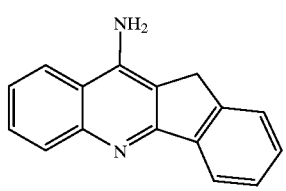
(2)

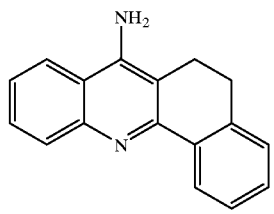
(3)

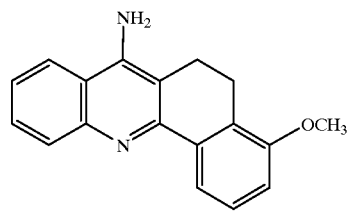
(4)

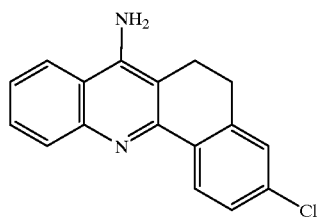
(5)

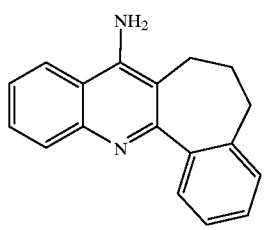
(6)

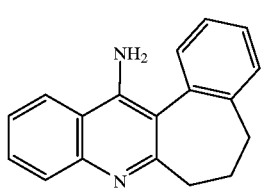
(7)

The anti-acetylcholinesterase and inhibition of noradrenaline and 5-HT uptake activity of compounds of general Formulae (I), (II), (II(a)) and (II(b)) has been demonstrated in a number of tests in vitro.

Particularly preferred compounds on the basis of their activity are compounds (1), (2) and (7), and physiologically functional derivatives thereof.

According to a further embodiment of the present invention there is provided a process for preparing compounds of general Formula (11(a)), which process comprises:

(A) Reacting anthranilonitrile (IV) with a benzosuberone (V).

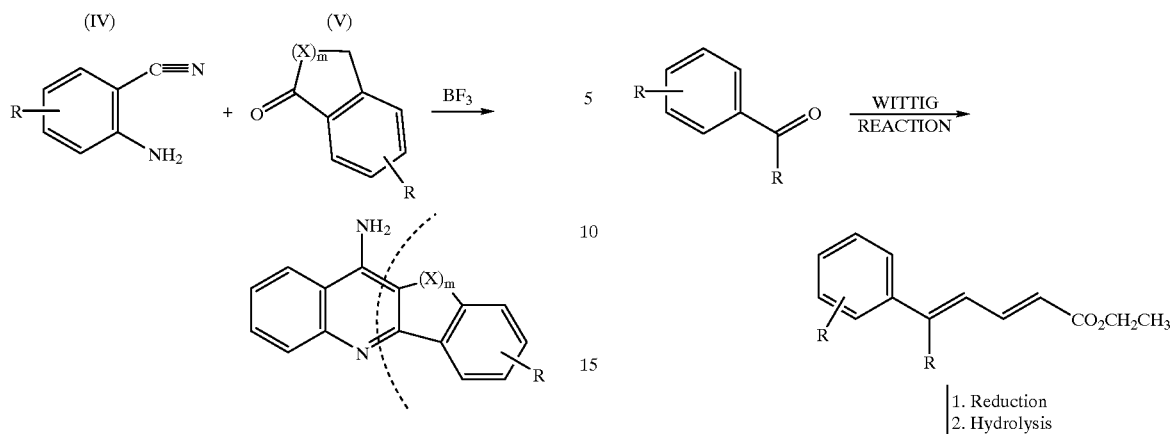

Anthranonitrile (IV) may be substituted with halogen e.g. Cl, Br, F, and alkoxy groups e.g. methoxy group. Benzosuberone (V) comprises group X which is —($CH_2$)— and m is a whole integer selected from 1, 2 and 3. Preferably, m is 2 or 3.

The benzosuberones (V) may be synthesised using substituted benzaldehydes (VI) and crotonic esters (VII) followed by reduction and cyclisation under reaction conditions employed in the art. An example of such a scheme is depicted below.

Thus the benzosuberone (V) can be prepared, for example, using halogen (e.g. F, Cl, Br) substituted or alkoxy substituted (e.g. methoxy substituted) benzaldehydes and crotonic esters followed by reduction and cyclisation reactions employed in the art as mentioned above.

To effect substitution at positions $C_7$, $C_8$, $C_6$, and $C_5$ of a benzosuberone the following strategies can be employed:

(i) For substitution in a 7 membered ring, the above synthesis can be adapted as follows:

i.e. variations (alkyl) at $C_9$ may be made wherein R is selected from $C_1$–$C_6$ alkyl, e.g. wherein R=$CH_3$.

(ii) Substitution at $C_8$ of benzosuberones can be made via one of two options:

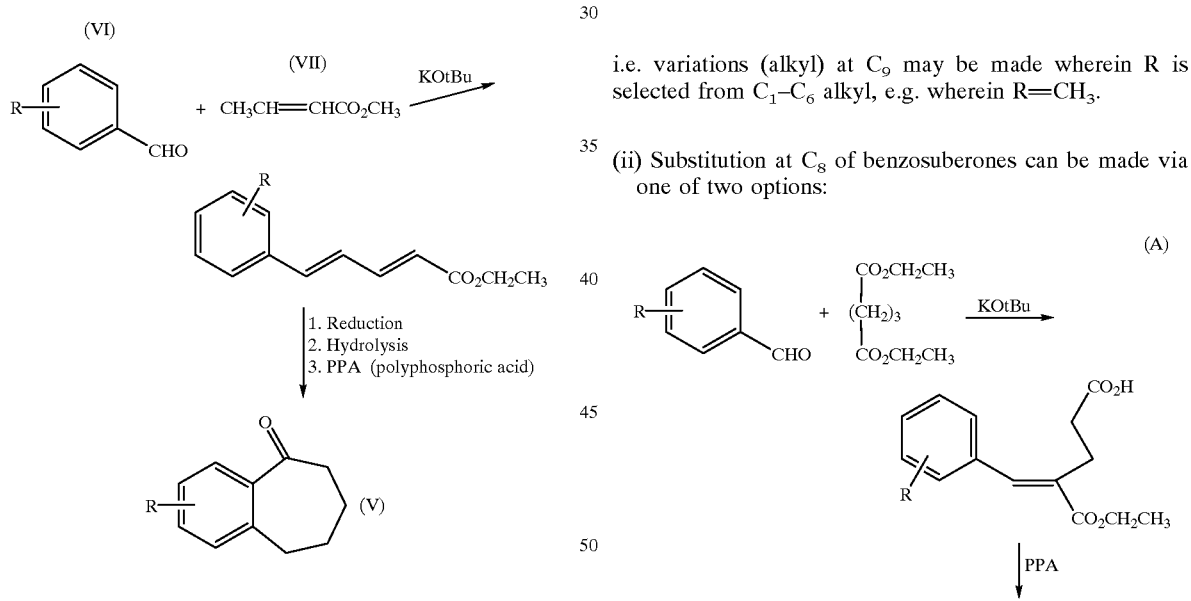

(B)

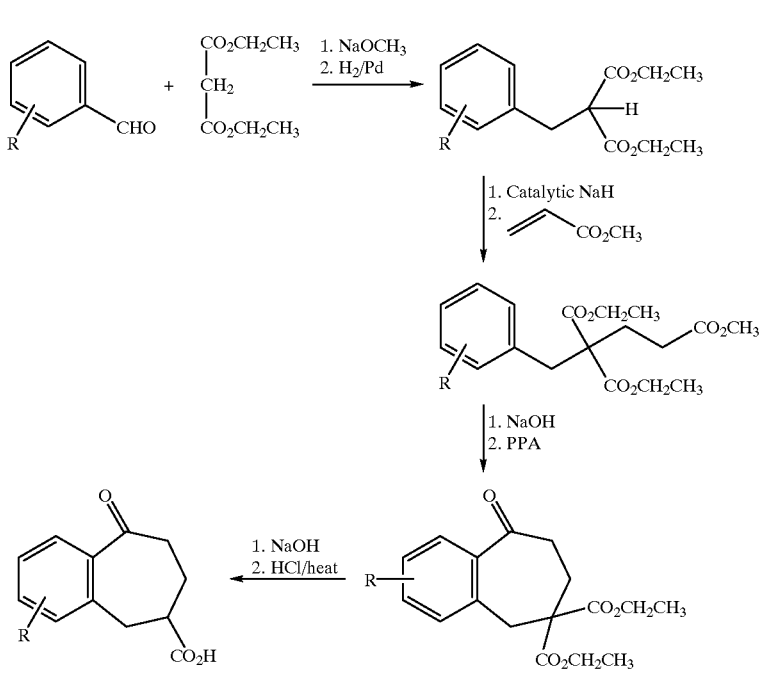

(iii) To effect substitution at $C_7$, a benzaldehyde is reacted with a substituted crotonate ester, such as

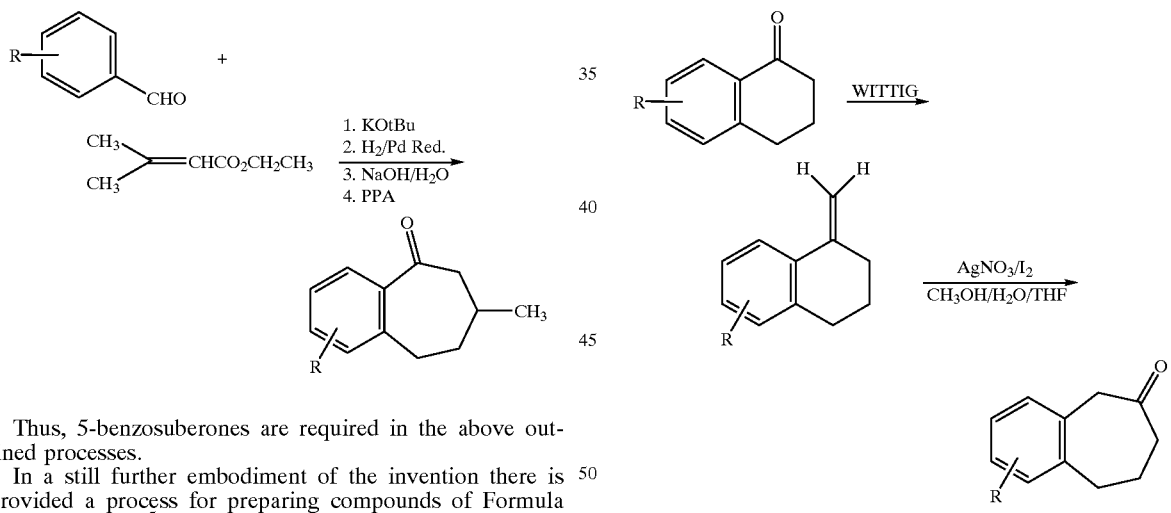

Thus, 5-benzosuberones are required in the above outlined processes.

In a still further embodiment of the invention there is provided a process for preparing compounds of Formula II(b), wherein $R^5=H$

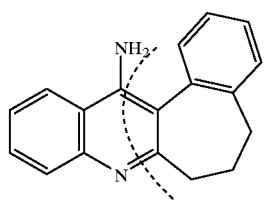

which process comprises:
(A) Reaction of anthranilonitrile (IV) with isomeric 6-benzosuberones. 6-benzosuberones are made using $C_1$–$C_6$ alkoxy substituted (e.g. methoxy) or halogen substituted, $C_1$–$C_6$ alkyl substituted, nitro substituted or carboxy-α-Tetralones in a ring expanding procedure as outlined hereinbelow:

Alternatively, certain molecules of Formula II may be synthesised in a number of steps by first condensing a suitable alkyl formate ester, such as an ethyl formate with an indanone, such as 1-indanone, and forming a hydroxymethylene indanone such as 2-hydroxymethylene-indan-1-one. This first condensation product can then be used in a further condensation reaction with a suitably substituted phenyl hydrazine hydrochloride, yielding a substituted pyrazole. Any substituents on the phenyl hydrazine employed may be located at the ortho, meta or para positions of the phenyl ring. Typically substituents are located in the para position. Suitable substituents which may be located on the phenyl ring include H, F, Cl, Br and $OCH_3$.

The substituted pyrazole can then be converted into a cyano-enamine using a suitable alkali metal hydride, such as sodium hydride in an appropriate organic solvent, such as boiling O-xylene. The resulting cyano-enamine can then be subjected to Lewis acid catalysis to produce a substituted molecule according to subgeneric formula (11(c)):

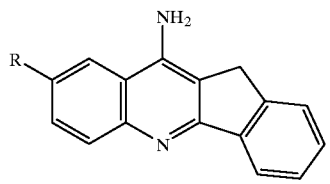
(II(c))

A reaction scheme illustrating the above outlined general procedure is shown below:

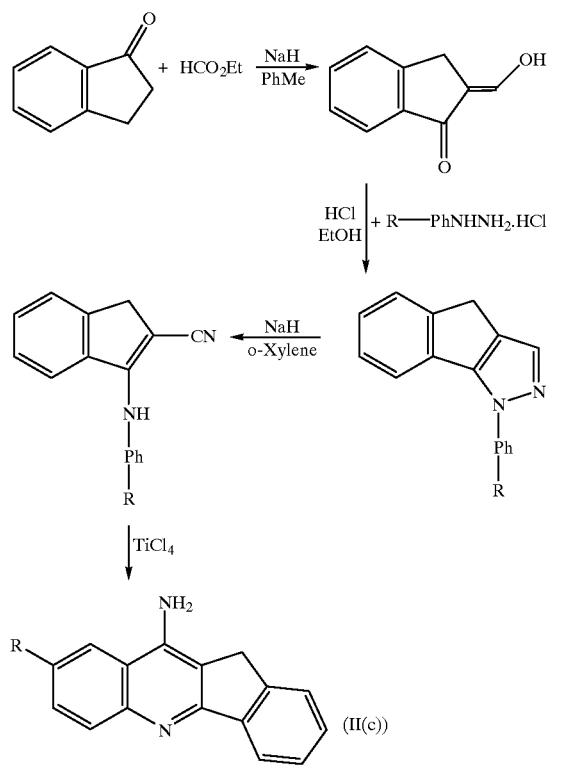

Naturally, the skilled addressee will appreciate that substituent R may be selected from H, Cl, Br, F and OCH₃.

Thus, in a further variant of the present invention there is provided a method for preparing a compound according to Formula (11(c)):

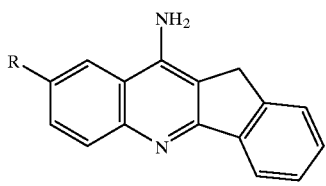

wherein
R is selected from H, F, Cl, Br and OCH₃; by
(i) condensing a 1-indanone with an alkyl formate forming a 2-OH methylene indan-1-one;
(ii) condensing the 2-OH-methylene indan-l-one with a phenyl hydrazine of Formula VIII:

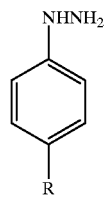
(VIII)

wherein
R is selected from H, F, Cl, Br, and OCH₃;
forming an indenopyrazole of Formula IX:

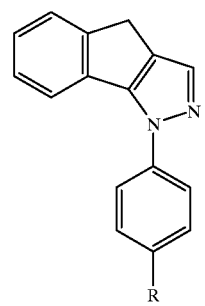
(IX)

(iii) opening the pyrazole ring and forming a phenyl amino cyano-1-indene of Formula X:

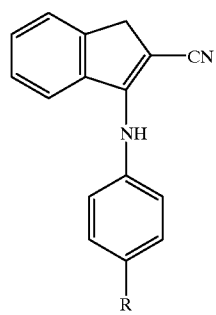
(X)

followed by Lewis base catalysis.

The skilled addressee will appreciate in step (i) that any base which is capable of catalysing nucleophilic addition to a 1-indanone yielding at least a 2-OH-methylene inden-1-one may be used in this step. Such bases generally have a pKa value of at least 16 and preferably more than 20. Such bases are generally soluble in aprotic solvents such as toluene (PhMe), tetrahydrofuran, diethyl ether, liquid NH₃, DMF, dimethoxy alkanes such as dimethoxy methane and dimethoxy ethane and the like. Suitable bases include alkali metal bases such as sodium or potassium alkoxides such as potassium tertiary butoxide, sodium ethoxide, sodium methoxide, sodium amide, KH, LiH, NaH, Lithium dialkyl amides such as Li-diazopropylamide, LiC(C₆H₅)₃, KC(C₆H₅)₃, and the like.

The alkyl formate may be any alkyl formate which is capable of condensation with the 1-indanone forming a 2-OH methylene inden-1-one. It is thought that the length of the alkyl arm may be of any length provided that the end product of step (i) is a 2-OH-methylene inden-l-one. For reasons of convenience the alkyl formate may be a $C_1$–$C_{10}$ alkyl formate, suitably a $C_1$–$C_6$ alkyl formate or more suitably a $C_1$–$C_3$ alkyl formate, such as ethyl formate.

In step (ii) the acidic species used in the reaction can correspond to the salt of the phenyl hydrazine used. Examples of suitable acidic species include hydrochloric acid, nitric acid, sulphuric acid as appropriate. Generally, any acid used should be capable of acid catalysed addition of phenyl hydrazine to 2-OH-methylene inden-1-one forming an indenopyrazole of Formula (IX).

In step (iii), the base catalysed opening of the pyrazole ring of the indenopyrazole (IX), and subsequent formation of the phenyl amino cyano-1-indene (X) should be conducted in a solvent with a suitably high boiling temperature such that ring opening can occur. A suitable solvent may be an aprotic solvent having a boiling point above about 140° C., such as O-xylene. The man skilled in the art will also appreciate that any Lewis acid catalyst may be used in the Lewis acid catalysed re-arrangement so long as a phenyl amino cyano-1-indene of Formula (X) is converted into a compound of Formula (II(c)).

Carboxy-α-tetralones may or may not be substituted with $C_1$–$C_6$ alkyl groups at position 2, 3 or 4.

Formula (III) may be viewed as:

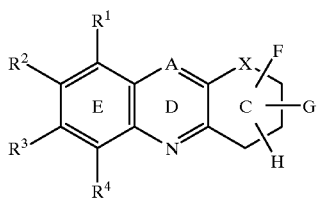

(III)

wherein $R^1$ is selected from $NH_2$, OH, H, F, Cl, Br, I, $OCH_3$, $C_1$–$C_6$ alkyl or aryl (phenyl);

$R^2$ is selected from H, $C_1$–$C_6$ alkyl, $C_1$–$C_6$ alkoxy, Cl, Br, F, I, and OH;

$R^3$ is selected from H, F, Cl, Br, I, OH, $OCH_3$ and $C_1$–$C_6$ alkyl;

$R^4$ is selected from H, F, Br, Cl, I, $OCH_3$, OH or $C_1$–$C_6$ alkyl;

A represents C—$NHR^9$ wherein $R^9$ is selected from H, $C_1$–$C_6$ alkyl or aryl;

X represents a carbon-carbon bond or represents —$(CH_2)_n$— wherein n is a whole integer selected from 1, 2 or 3; and a 5, 6, 7 or 8 carbon-membered unsubstituted ring can be optionally fused to Ring C at any one of faces F, G or H indicated on Ring C, with the proviso that when Ring C is a 5 or 6-carbon unsubstituted ring and is not fused at any of faces F, G and H at least one of $R^1$, $R^2$, $R^3$ and $R^4$ is not H.

Preferably, $R^1$ is selected from H, F. Cl, and $CH_3$;

$R^2$ is selected from H, Cl, F, Br, —$OCH_3$, NH, and $CH_3$;

$R^3$ is selected from H, F, Cl, and $CH_3$;

$R^4$ is selected from H, Cl, F, OH, and $CH_3$;

A represents C—$NHR^9$ wherein $R^9$ is selected from H and

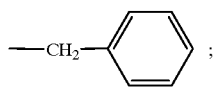

;

X represents a carbon-carbon bond or represents —$(CH_2)_n$— wherein n is 1; and a 6 membered carbon ring is optionally fused to Ring C at face H, with the proviso that when Ring C is a 5 or 6-carbon-membered unsubstituted ring and is not fused at any of faces F, G and H at least one of $R^1$, $R^2$, $R^3$ and $R^4$ is not H.

Naturally the skilled addressee will appreciate that free acid addition salts of compounds of Formula (III) are also encompassed within the present invention.

Suitable acid addition salts include those formed from hydrochloric, hydrobromic, nitric, perchloric, sulphuric, citric, tartaric, phosphoric, lactic, benzoic, glutamic, oxalic, aspartic, pyruvic, succinic, fumaric, maleic, oxaloacetic, isethionic, strearic, phthalic, methanesulphonic, p-toluene sulphonic, benzenesulphonic, lactobionic and glucuronic acids. Most preferably, the salts will be pharmaceutically acceptable.

Unless otherwise indicated, alkyl groups of $R^1$, $R^2$, $R^3$l $R^4$ and $R^9$ present in Formula (III) may be straight or branched chain alkyl groups such as isopropyl, propyl, butyl, isobutyl, tertbutyl and the like.

Preferred compounds according to Formula III on the basis of their activity include:

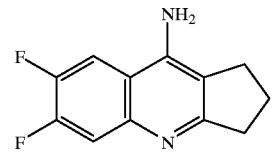

(8)

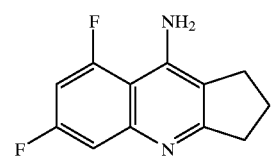

(9)

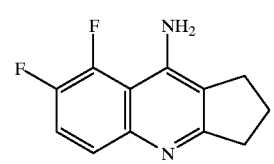

(10)

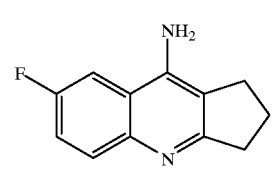

(11)

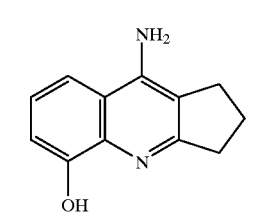

(12)

-continued

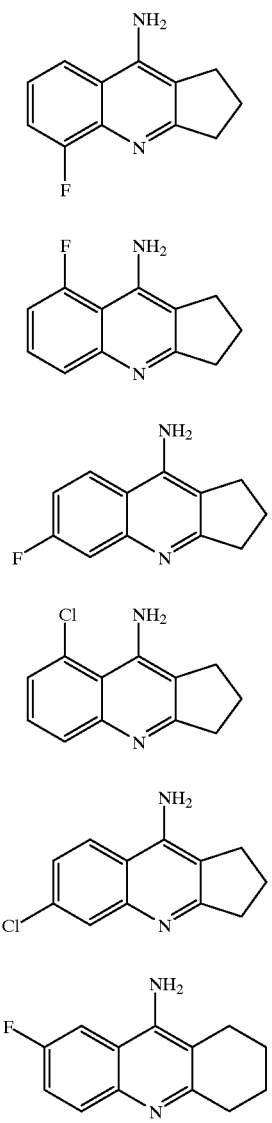

(13)

(14)

(15)

(16)

(17)

(18)

The anti-acetylcholinesterase and inhibition of 5-HT uptake and/or noradrenaline uptake activity of compounds of subgeneric Formula (III) has been demonstrated in a number of tests in vitro.

Particularly preferred compounds of subgeneric Formula (III) on the basis of their activity are (8), (10), (14), (16) and (17), and physiologically functional derivatives thereof.

According to a further embodiment of the present invention there is provided a process for preparing compounds of general Formula (III) which process includes the, synthesis of an α-cyano ketone, such as the one depicted below:

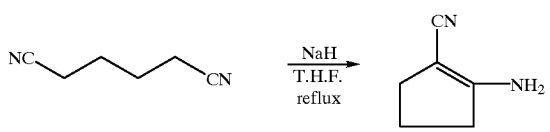

-continued

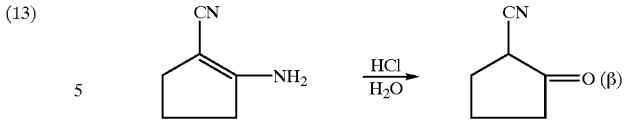

(β)

In this case, the α- cyano ketone, cyclopentanone-2-carbonitrile was synthesised by the Thorpe-Ziegler cyclisation of 1,4- dicyanobutane and subsequent hydrolysis, as outlined above.

Substituted or unsubstituted aniline compounds can then be condensed with cyano ketones according to the following general scheme and then converted to a tacrine derivative utilising Lewis acids:

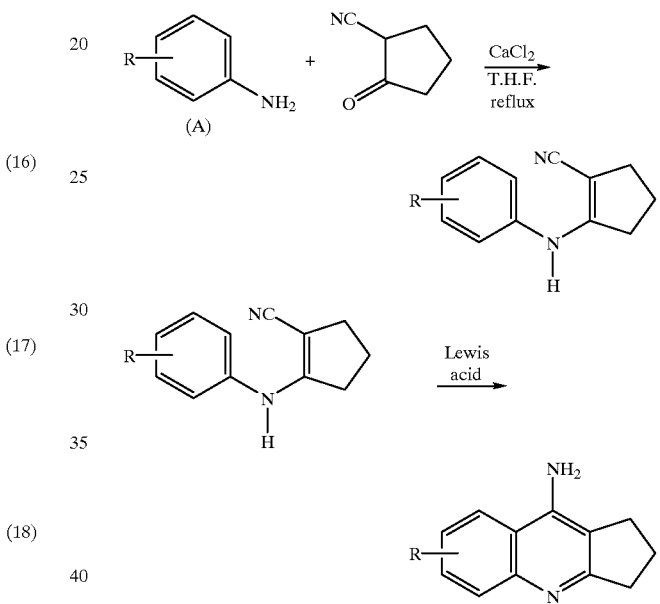

Examples of Lewis acids which can be used in the above scheme include $BF_3.O(CH_2CH_3)_2$, $AlCl_3$ and $TiCl_4$. Examples of independently selected substituents, R, which can be added forming aniline derivatives (A) include $CH_3$, OH, F, Br, Cl, and —$OCH_3$. Thus, there can be more than one R substituent on the aniline derivative (A).

In a further alternative, the α-cyano ketone can be a six membered α-cyano ketone which is also capable of being synthesised along similar lines as compound (B), thus:

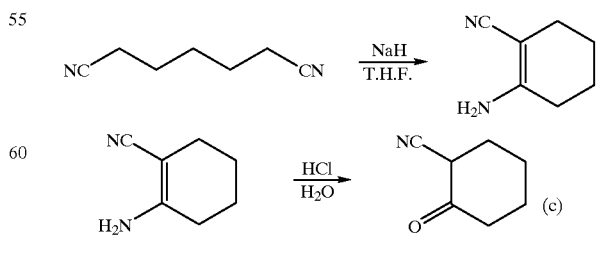

(c)

A fluoro-substituted aniline, in this case a 4-fluoro-substituted aniline can be condensed with cyano ketone (C).

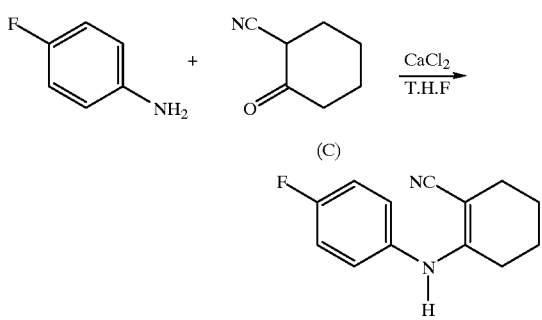

The resulting enamine is able to be cyclised to give a fluorinated tacrine analogue, such as exemplified below:

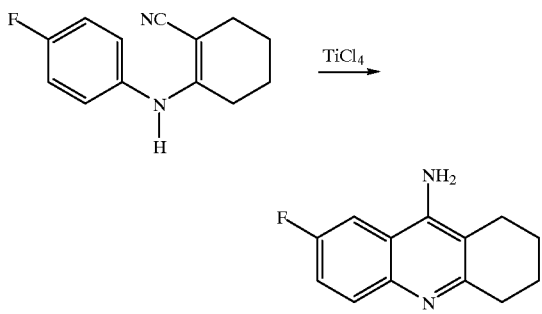

In a further alternative, the a-cyano ketone can be a benzo substituted derivative which can be synthesised along the following lines:

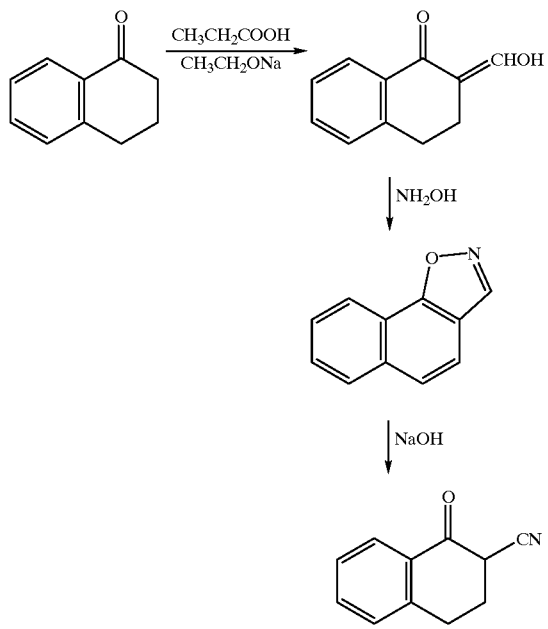

The α-cyano ketone can then be condensed with a substituted aniline, for example a fluoro-substituted aniline, forming an enamine which can then be cyclised using a Lewis acid, such as $TiCl_4$.

The compounds of the present invention are indicated as being useful in alleviating symptoms of Alzheimer's disease. They may be employed in treating various forms of organic or degenerative dementia.

The invention thus further provides a method for the treatment of Alzheimer's disease in humans, which comprises the administration of a clinically useful amount of a compound of Formula (I), (II) or (III) or a pharmaceutically acceptable salt or physiologically functional derivative in a pharmaceutically useful form, once or several times a day or in any other appropriate schedule, orally, rectally, or parenterally.

In addition, there is provided as a further, or alternative, aspect of the invention, a compound of Formula (I), (II) or (III) or a pharmaceutically acceptable salt or physiologically functional derivative thereof for use in therapy, for example in the treatment of Alzheimer's disease.

The amount of compound of Formula (I), (II) or (III) required to be effective in a treatment for degenerative dementia, such as Alzheimer's disease will, of course, vary and is ultimately at the discretion of the medical or veterinary practitioner. The factors to be considered include the condition being treated, the route of administration, and nature of the formulation, the mammal's body weight, surface area, age and general condition, and the particular compound to be administered. A suitable effective dose lies in the range of about 0.01 to about 120 mg/kg bodyweight, e.g. 0.1 to about 120 mg/kg bodyweight, preferably in the range of about 0.1 to 50 mg/kg, for example 0.5 to 5 mg/kg. The total daily dose may be given as a single dose, multiple doses, e.g., two to six times per day or by intravenous infusion for selected duration. For example, for a 75 kg mammal (e.g. a human) the dose range would be about 8 to 9000 mg per day, and a typical dose could be about 50 mg per day. If discrete multiple doses are indicated treatment might typically be 15 mg of a compound of Formula (I), (II) or (III) given up to 4 times per day.

Whilst it is possible for the active compound to be administered alone, it is preferable to present the active compound in a pharmaceutical formulation. Formulations of the present invention, for medical use, comprise a compound of Formula (I), (II) or (III) or a salt thereof together with one or more pharmaceutically acceptable carriers and optionally other therapeutic ingredients. The carrier(s) should be pharmaceutically acceptable in the sense of being compatible with the other ingredients of the formulation and not deleterious to the recipient thereof.

The present invention, therefore, further provides a pharmaceutical formulation comprising a compound of Formula (I), (II) or (III), or a pharmaceutically acceptable salt or physiologically functional derivative thereof together with a pharmaceutically acceptable carrier therefor.

There is also provided a method for the preparation of a pharmaceutical formulation comprising bringing into association a compound of Formula (I), (II) or (III), or a pharmaceutically acceptable salt or physiologically functional derivative thereof, and a pharmaceutically acceptable carrier therefor.

Formulations according to the present invention include those suitable for oral, topical, rectal or parental (including subcutaneous, intramuscular and intravenous administration. Preferred formulations are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredient. In general, the formulations are prepared by uniformly and intimately bringing the active compound into association with a liquid carrier or a finely divided solid carrier or both and then, if necessary, shaping the product into desired formulations.

Formulations of the present invention suitable for oral administration may be presented as discrete units as capsules, cachets, tablets or lozenges, each containing a predetermined amount of the active compound; as a powder or granules; or a solution or suspension in an aqueous or non-aqueous liquid such as a syrup, an elixir, an emulsion or a draught.

A tablet may be made by compression or moulding, optionally with one or more accessory ingredients. Compressed tablets may be prepared by compressing in a suitable machine the active compound in a free-flowing form such as a powder or granules, optionally mixed with a binder, lubricant, inert diluent, surface active or dispersing agent. Moulded tablets may be made by moulding in a suitable matching a mixture of the powdered active compound with any suitable carrier.

A syrup may be made adding the active compound to a concentrated, aqueous solution of a sugar, for example sucrose, to which may also be added any accessory ingredients. Such accessory ingredient(s) may include flavourings, an agent to retard crystallization of the sugar or an agent to increase the solubility of any other ingredients, such as a polyhydric alcohol for example glycerol or sorbitol.

Formulations for rectal administration may be presented as a suppository with a conventional carrier such as cocoa butter.

Formulations suitable for parenteral administration conveniently comprise a sterile aqueous preparation of the active compound which is preferably isotonic with the blood of the recipient. Such formulations suitably comprise a solution of a pharmaceutically and pharmacologically acceptable acid addition salt of a compound of Formula (I), (II) or (III), that is isotonic with the blood of the recipient.

Useful formulations also comprise concentrated solutions or solids containing the compound of Formula (I), (II) or (III), which upon dilution with an appropriate solvent give a solution for parenteral administration as above.

In addition to the aforementioned ingredients, the formulations of this invention may further include one or more accessory ingredient(s) selected from diluents, buffers, flavouring agents, binders, surface active agents, thickeners, lubricants, preservatives (including antioxidants) and the like.

In a further aspect of the present invention provides the use of a compound of Formula (I), (II) or (III) or a pharmaceutically acceptable salt or physiologically functional derivative thereof for the manufacture of a medicament for the treatment of degenerative brain disorders, such as Alzheimer's disease.

In a preferment there is provided use of a compound according to formula (I), (II) or (III) selected from compounds 1 to 18 as hereinabove described and compound 29:

(29)

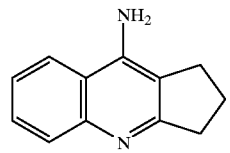

or a pharmaceutically acceptable salt or physiologically functional derivative thereof for the manufacture of a medicament for the treatment of degenerative brain disorders, such as Alzheimer's disease.

The invention will now be illustrated by the following non-limiting examples.

Examples Section i(i): Illustration of the Synthesis of Compounds of Formula II and Pharmacological Activity Thereof Equipment Melting points were obtained on a Gallenkamp melting point apparatus in open capillaries and are uncorrected.

$^1$H NMR spectra were recorded on a Perkin-Elmer R32 spectrometer operating at 90 MHz, on a Bruker SM250 spectrometer operating at 250.13 MHz, and on a Bruker AMX400 spectrometer operating at 400.13 MHz, with the WM250 and the AMX400 in Fourier Transform mode. J Values are given in Hertz. $^{13}$C spectra were recorded on a Bruker AMX400 operating at 100.62 MHz in Fourier Transform mode.

Infrared spectra were recorded on a Unicam Mattson 1000 series FTIR spectrometer as thin films, Nujol mulls or in solution cells.

Flash column chromatography was carried out using CAMLAB Art. Nr81538 MN Kieselgel 60 (0.040–0.063 mm) and Merck 7735 silica gel type 60 (0.125–0.250 mm) or on modified $C_{18}:C_1$ reverse phase silica gel$^R$. Samples were applied in the solution or adsorbed onto silica.

Mass spectra were obtained on a AEIMST double-focusing mass spectrometer, modified with a solid state console using a GEC 905 computer based data system.

Carbon, hydrogen and nitrogen analysis were determined on a Carlo Erba 1106 analyser using a technique based on the classical Pregl Dumas method.

Halogens were determined by combusting the sample in an oxygen flask containing hydrogen peroxide and potassium hydroxide and titrating an alcoholic solution of the products with mercuric nitrate using diphenylcarbazone as indicator (Mercurimetric method).

Sulphur was determined by combusting the sample in an oxygen flask containing hydrogen peroxide and water and titrating an alcoholic solution of the products with barium perchlorate using the mixed indicator THORON and methylene blue.

Toluene was dried over sodium; THF was pre-dried with anhydrous sodium sulphate and distilled over calcium hydride or sodium benzophenone ketyl.

All solutions were dried over anhydrous sodium sulphate or anhydrous magnesium sulphate and filtered.

Thin layer chromatography was carried out on plastic sheets precoated with 0.25 mm aluminium oxide also with fluorescent indicator $UV_{254}$, both supplied by CAMLAB.

General Procedure for the Cyclodehydration Reaction 2-amino-1-cyano-benzene, appropriate ketone (1.1 equivalents) and sodium-dried toluene (120 ml) were placed in a three-necked round-bottomed flask fitted with an overhead stirrer. Boron trifluoride diethyl etherate (1.1 equivalents) was added slowly via syringe and the reaction mixture heated at reflux for 24 hours. On cooling, the toluene was decanted and, to liberate the product, the remaining solids were treated with sodium hydroxide (2M, 120 ml) and heated at reflux for 24 hours. After cooling, the organic components were extracted with chloroform and the organic layers were combined, dried and the solvent evaporated in vacuo to give the desired product.

In each case, the compounds made were easily identifiable by TLC analysis where they showed as a characteristic near baseline spot (solvent; ethyl acetate).

In each case, a sample was recrystallised from the stated solvent for analysis.

EXAMPLE 1

6-Amino-4, 5-benzo-[5H]-cyclopenta-[1,2-b]-quinoline (2)

2-amino-1-cyano-benzene (Aldrich Chemicals) (4.6 g, 38.9 mmol), 2,3-dihydrobenzocyclopenten-[1H]-1-one (5.6 g, 42.4 mmol) (Aldrich Chemicals) and boron trifluoride diethyl etherate (1M, 5.3 ml, 43.3 mmol) were treated according to the general procedure described herein to give the title compound.

Recrystallised: m.p. (dec) 239–240° C. (EtOH). Found: C, 82.50; H, 5.2; N, 12.0; M$^+$ 232, 1006. $C_{16}H_{12}N_2$ requires C, 82.7; H, 5.2; N, 12.1%; M$^+$, 232.1000. δH(250 MHz, CD$_3$OD) 3.78 (2H, s, CH$_2$,), 7.20–7.69 (5H, m, aryl-H), 7.94 (1H, d, J=8.5, aryl-H), 8.03 (1H, d, J=8.4, aryl-H), 8.10–8.25 (1H, m, aryl-H). Maleate salt m.p. 212–214° C. Found: C, 68.6; H, 4.5; N, 7.9, $C_{16}H_{12}N_2$. $C_4H_4O_4$ requires C 68.95; H, 4.6; N, 8.05%. δH(250 MHz, DMSO-d$_6$) 3.91 (2H, s, CH$_2$), 2.60–4.70 (2H, br s, exchanges with D$_2$O, NH$_2$), 6.06 (2H, s, maleate), 7.50–8.00 (6H, m, aryl-H), 8.18 (1H, d, J=7.2, aryl-H), 8.43 (1H, d, J=8.4, aryl-H), 8.71 (2H, br, s, exchanges with D$_2$O, maleate).

EXAMPLE 2

7 Amino-5, 6-dihydro-benz-[c]-acridine (3)

2-amino-1-cyano-benzene (2.0 g, 16.9 mmol), α-tetralone (3, 4-dihydro-[2H]-naphthalene-1-one) (Aldrich Chemicals) (2.7 g, 18.5 mmol) and boron trifluoride diethyl etherate (1M, 2.3 ml, 18.8 mmol) were treated according to the general procedure described herein to give the title compound.

Recrystallised: m.p. 138–140° C. (EtOH). Found: C, 83.1; h, 5.8; n, 11.3; M$^+$, 246.1159. $C_{17}H_{14}N_2$ requires C, 82.9; H, 5.7; N, 11.3%; M$^+$, 246.1157. δH (90 MHZ, CDCl$_3$) 2.6–3.1 (4H, m, 2CH$_2$), 4.55 (2H, br s, exchanges with D$_2$O, NH$_2$), 7.10–7.80 (6H, m, aryl-H), 8.00–8.20 (1H, m, aryl-H), 8.5–8.7 (1H, m, aryl-H). Maleate Salt m.p. 207–209° C. Found: C, 69.90; H, 4.8; N, 7.6; $C_{17}H_{14}N_2$. $C_4H_4O_4$ requires C, 69.6; H, 5.0; N, 7.7% δH (250 MHz, CD$_3$OD) 2.7–3.2 (4H, m, CH$_2$), 6.22 (2H, S, maleate), 7.3–7.7 (4H, m, aryl-H), 7.87 (1H, t, J=7.3, aryl-H), 7.95–8.2 (2H, m, aryl-H), 8.35 (1H, d, J=7.6, aryl-H).

EXAMPLE 3

7-Amino-5, 6-dihydro-4-methoxybenz-[c]-acridine (4)

2-amino-1-cyano-benzene (5.0 g, 42.3 mmol), 3, 4-dihydro-5-methoxy-[2H]-napthalen-1-one) (Aldrich Chemicals) (8.1 g, 46.0 mmol) and boron trifluoride diethyl etherate (1M, 5.7 ml, 46.6 mmol) were treated according to general procedure described herein to give the title compound.

Recrystallised: m.p. 126–129° C. (CHCl$_3$). Found: C, 78.3; H, 5.65; N, 10.0; M$^+$, 276.1265. $C_{18}H_{16}N_2O$ requires C, 78.2; H, 5.8; N, 10.1%; M+, 276.1263. δH (90 MHz, CDCl$_3$) 2.5–3.2 (4H, m, 2CH$_2$), 3.9 (3H, s, CH$_3$), 4.6 (2H, br, s, exchanges with D$_2$O, NH$_2$), 6.8–7.0 (1H, d, J=9, aryl-H), 7.2–7.8 (2H, m, aryl-H), 8.0–8.35 (1H, m, aryl-H). Maleate salt m.p. (dec) 210–216° C. Found: C, 67.3; H, 5.0; N, 7.1; $C_{18}H_{16}N_2O$. $C_4H_4O_4$ requires C, 67.35; H, 5.1; N, 7.1%. δH (250 MHz, DMSO-d$_6$) 2.70–3.05 (4H, m, CH$_2$), 3.89 (3H, s, CH$_2$), 3.06 (2H, s, maleate), 7.29 (1H, d, J=8.1, aryl-H), 7.52 (1H, t, J=8.0, aryl-H), 7.64 (1H, t, J=7.3, aryl-H), 7.81 (1H, d, J=7.8, aryl-H), 7.90 (1H, t, J=7.4, aryl-H), 7.13 (1H, d, J=8.3, aryl-H), 8.45 (1H, d, J=8.3, aryl-H), 8.57 (2H, br s, maleate).

EXAMPLE 4

7-Amino-5, 6-dihydro-3-chlorobenz-[c]-acridine (5)

2-amino-1-cyano-benzene (5.0 g, 42.3 mmol), 6-chloro-3, 4-dihydro-[2H]-napthalen-1-one (Organon Laboratories) (8.8 g, 48.7 mmol) and boron trifluoride diethyl etherate (1M, 6.4 ml, 52.4 mmol) were treated according to the general procedure described herein to give the title compound.

Recrystallised: m.p. 205–208° C. (EtOH). Found: C, 73.0; H, 4.6; N, 10.3; M$^+$, 280.0769. $C_{17}H_{15}N_2Cl$ requires C, 72.7; H, 4.7; N, 10.0%; M$^+$, 280.0767 δH (90 MHz, CDCl$_3$) 2.7–3.1 (4H, m, 2CH$_2$), 4.6 (2H, br s, exchanges with D$_2$O, NH$_2$), 7.1–8.2 (6H, m, aryl-H), 8.5 (1H, d, J=8.1, aryl-H). Maleate salt m.p. (dec.) 220–221° C. Found: C, 63.7; H, 4.05; N, 6.9; Cl, 9.1. $C_{17}H_{15}N_2Cl$. $C_4H_4O_4$ requires C, 63.6; H, 4.3; N, 7.05; Cl, 8.9%. δH (2.50 MHz, DMSO-d6) 2.30–3.06 (4H, m, 2CH$_2$), 3.34 (2H, br s, NH$_2$), 6.05 (2H, s, maleate), 7.55–7.70 (3H, m, aryl-H), 7.88 (1H, t, J=7.9, aryl-H), 8.07 (1H, d, J=8.5, aryl-H), 8.19 (1H, d, J=8.1, aryl-H), 8.43 (1H, d, J=8.3, aryl-H), 8.51 (2H, br s, maleate).

EXAMPLE 5

8-Amino-6, 7-dihydro-5H-benzo-[6, 7] cyclohepta [1, 2-b] quinoline (6)

2-amino-1-cyano-benzene (2.0 g, 16.9 mmol), 1-benzosuberone (6, 7, 8, 9-tetrahydrobenzocyclohepten-5-one) (3.0 g, 18.7 mmol) and boron trifluoride diethyl etherate(1M, 2.6 ml, 18.7 mmol) were treated according to the general procedure described herein to give the title compound.

Recrystallised: m.p. 190–192° C. (EtOH). Found: C, 83.5; H, 6.1; N, 10.6; M$^+$, 260.1304. $C_{18}H_{16}N_2$ requires C, 83.15; H, 6.2; N, 10.8%; M$^+$, 260.1313. δH (90 MHz-d6): 1.9–2.8 (6H, m, 3CH$_3$), 6.55 (2H, br s, exchanges with D$_2$O, NH$_2$), 7.1–7.95 (7H, m, aryl-H), 8.2–8.35 (1H, m, aryl-H). Maleate salt m.p. 186–188° C. Found: C, 70.2; H, 5.4; N, 7.4 $C_{18}H_{16}N_2C_4H_4O_4$ requires C, 70.2; H, 5.35; N, 7.4% δH (250MHz, CD$_3$OD) 2.25 (2H, br s, CH$_2$), 2.63 (2H, br s, CH$_2$), 5.07 (2H, br s, CH$_2$), 6.19 (2H, s, maleate), 7.35–8.05 (7H, m, aryl-H), 8.35 (1H, d, J=8.4, aryl-H).

EXAMPLE 6

13-Amino-1,2 dihydro-5-methoxy[1H] benz [7] annuleno [5,4-b] quinoline (1)

2-amino-1-cyano-benzene (5.0 g, 42.3 mmol), 6, 7, 8, 9-tetrahydro-2-methoxy-5H-benzocyclohepten-5-one (synthesised according to the method of Khan A. M. et al., J. Chem Soc., (1966) p. 990) (8.7 g, 45.8 mmol) and boron trifluoride diethyl etherate (1M, 6.2 ml, 50.7 mmol) were treated according to the general procedure described herein to give the title compound.

Recrystallised: m.p. 206–210° C. (EtOH). Found: C, 78.9; H, 6.4; N, 9.6; M$^+$, 290.1419, $C_{19}H_{18}N_2O$ requires C, 78.60; H, 6.2; N, 9.6%; M$^+$, 290.1419. δH (90 MHz, DMSO-d6) 1.8–2.8 (6H, m, 3CH$_3$), 3.85 (3H, s, CH$_3$), 6.5 (2H, br s, exchanges with D$_2$O, NH$_2$), 6.75–8.4 (7H, m, aryl-H). Maleate salt m.p. 216–218° C. Found: C, 67.6; H, 5.2; N, 6.6. $C_{19}H_{18}N_2O$. $C_4H_4O_4$ requires C, 68.0; H, 5.45; N, 6.9%. δH (250 MHz, CD$_3$OD) 2.20–2.75 (6H, m, 3CH$_3$), 3.89 (3H, s, CH$_3$), 6.21 (2H, s, maleate), 6.95–7.10 (2H, m, aryl-H), 7.60–7.72 (2H, m, aryl-H), 7.85–7.95 (2H, m, aryl-H), 8.35 (1H, d, J=8.7, aryl-H).

EXAMPLE 7

13-Amino 6.7 dihydro[1H] benz [7] annuleno [4,5-b]quinoline (7)

Anthranilonitrile (1.0 g, 8.5 mmol), 6, 7, 8, 9-tetrahydro-5H-benzocyclo-hepten-6-one (El-Hossini M. S. et al., Tetrahedron Lett., (1986) 27, p.3783) (1.5 g, 9.4 mmol) and boron trifluoride diethyl etherate (1M, 1.2 ml, 9.8 mmol) were treated according to the general procedure (pg. 29) to give the title compound.

Recrystallised: m.p. 177–179° C. (CH$_3$CH$_2$OH). Found: C, 82.85; H, 6.4; N, 10.55; M$^+$, 260.1315. C$_{18}$H$_{16}$N$_2$ requires C, 83.05; H, 6.2; N, 10.75%; M$^+$, 260.1314. δH (250 MHz, CDCl$_3$) 2.08–2.68 (5H, m); 2.82–2.90 (1H, m); 4.96 (2H, br s, exchanges with D$_2$O, NH$_2$); 7.34–7.66 (6H, m, aryl-H), 7.79 (1H, d, J=8.35, aryl-H), 7.00 (1H, d, J=8.43, aryl-H).

EXAMPLE 7(a)

1, 2, 3, 4-Tetrahydro-1-methylene-napthalene (Intermediate Leading to Compound 33)

N-Butyl lithium (Aldrich) (47 cm$^3$, 74.8 mmol, 1.6 M solution in hexane) was added dropwise to a solution of methyl triphenylphosphonium iodide (Aldrich) (27.65 g, 68 mmol) in dry THF (150 cm$^3$), under nitrogen at 0° C. α-Tetralone (Aldrich) (10 g, 68 mmol) in dry THF (100 cm$^3$ was then added dropwise and the mixture stirred for 17 hours at room temperature. The reaction mixture was then added to water and extracted with ethyl acetate. The combined extracts were then dried (Na$_2$SO$_4$), filtered and concentrated in vacuo. Purification was by column chromatography on a neutralised silica column (Et$_3$N) (Eluant: Pet. Ether 40–60° C.) produced a colourless mobile oil.

δ$_H$ (250 MHz, CDCl$_3$), 1.95 (2H, m, CH$_2$), 2.6 (2H, m, CH$_2$), 2.88 (2H, t, J 6.3 Hz, CH$_2$), 4.99 (1H, dd, J 1.4, 2.7 Hz, vinyl (C—H), 5.51 (1H, d, J 1.1 Hz, vinyl (C—H), 7.1–7.3 (3H, m, aryl), 7.65–7.7 (1H, m, aryl). vmax (LF)/cm$^{-1}$ 3085, 3066, 3028, 3017 (Ar-Hstr), 2990, 2937, 2862, 2836 (C—H str), 1627 (C=C str).

EXAMPLE 7(b)

5, 7. 8, 9-Tetrahydro-[6H]-benzocyclohepten-6-one (Intermediate Leading to Compound 33)

1, 2, 3, 4-Tetrahydro-1-methylene-naphthalene (Example 1(a)) (1 g, 6.934 mmol) in THF (22 cm$^3$) was added to a vigorously stirring solution of silver nitrate (2.356 g, 13.87 mmol), water (26 cm$^3$) and methanol (26 cm$^3$). This was followed by immediate addition of iodine (1.76 g, 6.9 mmol). After stirring for 1 hour, precipitated silver iodide was removed by filtration and the liquors concentrated in vacuo. Purification was by column chromatography (Eluent: 15% ethyl acetate/N-hexane) and Kugelrohr distillation produced a mobile yellow oil (75° C., 0.05 mmHg).

Found : C, 81.81; H, 7.55% Calc. for C$_{11}$H$_{12}$O: C, 82.46; H, 7.55% δ$_H$ (250 MHz, CDCl$_3$) 2.00 (2H, quin, J 6.6 Hz, 4-H), 2.58 (2H, t, J 6.9 Hz, 5-H), 2.96 (2H, t, J 6.3 Hz, 3H), 3.63 (2H, s, 1-H), 7.05–7.3 (4H, m, aryl). vmax (LF)/cm$^{-1}$: 3064, 3019 (Ar—H str), 2936, 2862 (Aliph C—H str), 1708 (C=Ostr).

EXAMPLE 7(c)

13-Amino-6, 7-dihydro [1H] benz [7] annuleno [4, 5-b] quinoline (7) and 13-amino 1, 2-dihydro [1H] benz [7] annuleno [2, 3-b] quinoline (33)

Boron trifluoride diethyl etherate (1M, 0.89 g, 0.78 cm$^3$, 6.24 mmol) was added to a stirring solution of 5, 7, 8, 9-tetrahydro-[6H]-benzocyclohepten-6-one (Example 1(a) (ii)) (1.0 g, 6.24 mmol) anthranilonitrile (0.67 g, 5.67 mmol) and dry toluene (50 cm$^3$) and then heated under reflux for 19 hours. After cooling, the toluene was decanted and 2M NaOH (50 cm$^3$) was added and heated under reflux for 18 hours. After cooling, the reaction mixture was extracted with dichloromethane. The combined organic extracts were dried (Na$_2$SO$_4$), filtered and concentrated in vacuo to afford a brown solid. Purification was by column chromatography [Eluant: dichloromethane: ethanol: ammonia (200:8:1)] afforded two products. Kugelrohr distillation of the first fraction (180° C., 0.01 mmHg) produced an off-white solid (7). The second component was also distilled (225° C., 0.01 mmHg) to give a colourless solid (33).

(i) Compound 7: m.p. 187–188° C. Found : C, 82.9; H. 6.1; N, 10.85% C$_{18}$H$_{16}$N$_2$ requires: C, 83.05; H, 6.2; N. 10.8% δH [250 MHz, (CD$_3$)SO] 2.08 (2H, m, 6-H), 2.34 (2H, m, 7-H) , 2.63 (2H, m, 5-H), 6.23 (2H, br s, NH$_2$), 7.25–7.45 (4H, m, aryl), 7.54 (1H, dd, J 2.6, 9.8 Hz, aryl), 7.60 (1H, dd, J 1.2, 7.4 Hz, aryl), 7.77 (1H, dd, J 0.9, 8.4 Hz, aryl), 8.27 (1H, d, J 8.3 Hz, aryl). vmax (NUJOL)/cm$^{-1}$: 3469, 3295 (N—H str), 3092, 3054 (Ar—H str), 1642, 1566, 1498, 1430 (C=C str).

(ii) Compound 33: m.p. 250–252° C. (dec.).

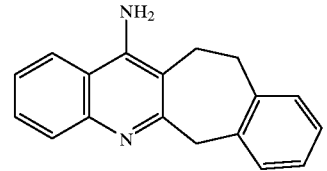

Found :C, 83.1; H, 6.1; N, 10.8% C$_{18}$H$_{16}$N$_2$ requires C, 83.05; H, 6.2; N, 10.2% δ$_H$[250 MHz, (CD$_3$)SO] 2.93 (2H, t, J 6.5 Hz, 10-H), 3.22 (2H, t, J 6.5 Hz, 11-H), 4.34 (2H, s, 5-H), 6.40 (2H, br s, NH,), 7.05–7.35 (5H, m, aryl), 7.49 (1H, dd, J 7.0, 8.1 Hz, aryl), 7.68 (1H, d, J 8.4 Hz, aryl), 8.14 (1H, d, J 8.4 Hz, aryl). vmax (NUJOL)/cm$^{-1}$: 3480, 3311 (N—H str), 3168 (Ar—H str), 1647, 1573 (C=C str).

EXAMPLE 8

Pharmacology

Four assays were employed to measure biological activity:

Inhibition of Acetylcholinesterase uptake activity (AChE)
Inhibition of Butyrylcholinesterase activity (BChE)
Inhibition of 5-HT (serotonin) uptake.
Inhibition of noradrenaline uptake (NA).

The biological activity of primary interest was that of AChE and 5-HT uptake. BChE uptake was measured such that compounds selective for AChE could be located. Inhibition of noradrenaline uptake was measured since compounds having the ability to potentiate transmission involving noradrenaline as well as 5-HT and acetylcholine are of interest.

EXAMPLE 8(A)

Anti-acetylcholinesterase Assay

The anticholinesterase assay is based on the method of Ellman et al., (Biochem. Pharmac. (1961) 7 pp88–95) by measuring the activity of AChE in the following coupled reactions:

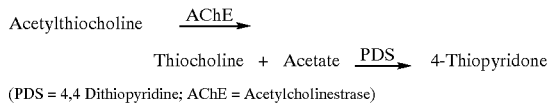

(PDS = 4,4 Dithiopyridine; AChE = Acetylcholinestrase)

Absorption max is at 324 nm.
(i) Enzyme Source for AChE
The following method of isolating the enzyme is essentially a modification of the method of Rotundo R. L. (1984) J. Biol. Chem 259 (21) pp. 13186–13194. 5 Male Rats (Sprague Dawley) weighing approx 250 g were killed by $CO_2$ overdose and cervical dislocation.

The brain was removed and homogenised (9 strokes at 840 rpm with 4 volumes of phosphate buffer pH 7.4+10 mM (EDTA) and centrifuged at 27,000 g for 30 minutes.

The supernatant was discarded and the pellet resuspended in phosphate buffer with 10 mM EDTA+1- Triton X100 (2 ml/g wet weight). The crude homogenate was centrifuged at 27,000 g for 30–40 minutes.

The pellet was discarded and the supernatant was dispensed into 0.5 ml aliquots and stored at −20° C. until required.
Phosphate Buffer (0.1M. pH 7.4)
$Na_2HPO_4$–5.75 g
$NaH_2PO_4 2H_2O$–1.48 g
Made up to 500 ml with distilled $H_2O$, pH 7.4.
Acetylthiocholine-5.2 mM (3.07 mg/2 ml phosphate buffer)
PDS-21 mM
(ii) Assay Procedure
0.5 ml aliquots of brain (enzyme solution) as prepared above were thawed out. 2 ml of phosphate buffer was added to each aliquot. 2 ml of the enzyme solution was incubated with 2 ml PDS for 60 minutes at 0° C. The composition of blank, control and test solutions are given below:
Blank
0.9 ml phosphate buffer (0.1 M, pH 7.4)
0.1 ml enzyme, PDS soln
Control
0.85 ml phosphate buffer (0.1M, pH 7.4)
0.1 ml enzyme, PDS soln
0.05 ml acetylthiocholine (5.2 mM)
Presence of Inhibitor
0.8 ml phosphate buffer (0.1M, pH 7.4)
0.1 ml enzyme, PDS soln
0.05 ml Acetylthiocholine 5.2 mM
0.05 ml inhibitor (Examples 1–7) to give final concentrations of 1, 3, 10, 30, 100, 300 nM; 1, 3, 10, 30, 100 $\mu$M.
Change in absorbance was measured at 30 second intervals for 3 minutes at 324 mm. The control was taken as 100%. Inhibitor was calculated as a percentage of the control. A graph of Log of inhibitor conc. versus % control was plotted and $IC_5$. values calculated by interpolation. Results are shown in Table I.

EXAMPLE 8(B)

Anti-butyrylcholinesterase Assay

The anticholinesterase assay is based on measuring the activity of BChE in the following coupled reactions:

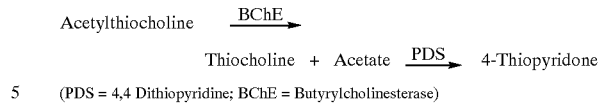

(PDS = 4,4 Dithiopyridine; BChE = Butyrylcholinesterase)

(i) Enzyme Source: BChE (Sigma product c-7512) 2.5 mg/ml phosphate buffer with 1% Triton X100 was made fresh for each experiment. The following components were utilised:
Phosphate Buffer (0.1M, pH 7.4)
$Na_2HPO_4$ 5.75 g
$NaH_2PO_4 2H_2O$ 1.48 g
Made up to 500 ml with distilled $H_2O$, pH 7.4
Acetylthiocholine 5.2 mM (3.07 mg/2 ml phosphate buffer)
PDS 21 mM (2.31 mg in 1 ml $CH_3CH_2OH$, plus 4 ml phosphate buffer)
(ii) Assay Procedure
1 ml of enzyme solution (i), was incubated with 2 ml PDS for 60 minutes at 0° C.
Components of the assay blank, controls and test solutions are provided below:
Blank
0.9 ml phosphate buffer (0.1M, pH 7.4)
0.1 ml enzyme PDS soln
Control
0.85 ml phosphate buffer (0.1 M, pH 7.4)
0.1 ml enzyme, PDS soln
0.05 ml Acetylthiocholine (5.2 mM)
Presence of Inhibitor
0.8 ml phosphate buffer (0.1M, pH 7.4)
0.1 ml enzyme PDS soln
0.05 ml Acetylthiocholine (5.2 mM)
0.05 ml inhibitor (Examples 1–7) to give final concentrations of 1, 3, 10, 30, 100, 300 nM; 1, 10, 30, 100$\mu$M.
Change in absorbance was measured at 30 second intervals at 324 nm. Control was taken as 100%. Inhibitor was calculated as a percentage of control. A graph of Log of inhibitor conc. versus % control was plotted and $IC_{50}$ values calculated by interpolation.
Results are shown in Table I.

EXAMPLE 8(C)

Monoamine Uptake Inhibition Assay
(i) Synaptosomal Preparation
One male rat (Sprague Dawley) weighing approx. 200–250 g was sacrificed by cervical dislocation. The brain was dissected out and the cerebellum discarded. The brain was then weighed and 10 ml ice cold sucrose (0.32M) added per gram tissue. The brain was then homogenised with a Teflon pestle (clearance 0.16 mm) at 840 rpm for 8 up-and-down strokes and then centrifuged at 100 g for 10 minutes at 4° C. The pellet was discarded and the supernatant retained (crude synaptosomal preparation).
(ii) Monoamine Uptake Inhibition Assay (5-HT and NA)
The assay was based on a method as described by Snyder and Coyle (1969) J. Pharm. Exp. Ther. 165, 78–86 and Horn et al (1973) J. Neurochem 21, pp 883–888.
Control
2 ml Krebs buffer
Non-Specific Uptake
5-HT-determined by 10 $\mu$M fluoxetine (2 ml) (Eli Lilly Limited). NA-determined by 1 $\mu$M desipramine (2 ml) (Sigma Chemical Co.)
Presence of Inhibitor
Various concentrations of inhibitor(i.e. from Examples 1–7) to be tested (1, 3, 10, 30, 100, 300 nM; 1, 3, 10, 30, 100 $\mu$M) for uptake inhibition of monoamines (2 ml).

Krebs Henseleit Buffer

To make 1 liter:

| | | |
|---|---|---|
| NaCl | 6.92 g | 118.9 mM |
| KCl | 0.35 g | 4.69 mM |
| MgSO$_4$7H$_2$O | 0.29 g | 1.18 mM |
| CaCl$_2$ | 1.25 ml | 1.25 mM |
| KH$_2$PO$_4$ | 0.16 g | 1.17 mM |
| NaHCO$_3$ | 2.1 g | 24.99 mM |
| Glucose | 2.0 g | 11.1 mM |
| Ascorbic Acid | 0.2 g | 1.1 mM |
| EDTA | 0.05 g | 0.13 mM |
| Nialamide | 3.279 mg | 12.5 µg |

All tubes were set up in triplicate. 2 ml of Krebs buffer (above), non-specific uptake inhibitor or drug (i.e. Examples 1–7) to be tested was incubated in a shaking water bath at 37° C. 100 µl of the prepared synaptosomal preparation was added to each tube and incubated for 5 minutes in a shaking water bath at 37° C. Any reaction was stopped by plunging the tubes into an ice water bath. $^3$H NA ($10^{-7}$M) or $^3$H 5-HT ($10^{31}$ $^7$M) was added to each tube and incubated for 5 minutes in a shaking water bath at 37° C. Any reaction was stopped by plunging the tubes into an ice-water bath. Accumulated monoamines were collected using a Brandell Cell Harvester under mild vacuum. Filters were rinsed (2×) using 4 ml of ice-cold 0.9% saline. Scintillation fluid was added (4 ml/tube). Radioactivity was measured on a scintillation counter.

Non-specific values were subtracted from total values. The control was taken as 100%. Drug effects were calculated as a percentage of control inhibitor value. A graph of log of drug concentration versus % control was plotted and IC$_{50}$ values were calculated by interpolation.

Results are shown in Table 1.

TABLE 1

| | | IC50#µM(±SEM, n = 5) | | | |
|---|---|---|---|---|---|
| COMPOUND | FORM | 5HT UPTAKE | NA | AChE | BChE |
| (1) | BASE | 0.7 | 3.6 | 68.8 (4.2) | % C72 AT 100 µM |
| | SALT | 0.02 | 1.8 | 17.4 (0.094) | 34.4 (6.7) |
| (2) | SALT | 2.2 | 2.3 | 0.35 (0.059) | 3.1 (0.40) |
| (3) | BASE | 4.6 | 12.1 | 37.4 (2.9) | 3.3 (0.056) |
| | SALT | 2.0 | 13.2 | 7.8 (0.6) | 3.8 (0.60) |
| (4) | BASE | 5.8 | 1.4 | 47.5 (2.9) | 10.3 (0.70) |
| | SALT | 2.1 | 12.2 | 17.1 (0.99) | 1.9 (0.15) |
| (5) | BASE | 14.3 | 4.1 | 144.1 (7.3) | NO BLOCK AT 100 |
| | SALT | 5.2 | 6.1 | 17.93 (1.4) | 7.1 (8.2) |
| (6) | BASE | 4.7 | ND | 328.5 (53.7) | 36.0 (9.0) |
| | SALT | 1.0 | 1.9 | 17.5 (0.38) | 4.0 (0.57) |
| (7) | BASE | 0.02 | ND | 38.2 (8.1) | 26.4 (0.44) |

Examples Section 1(ii): Illustration of the Synthesis of Compounds of Formula (11(c)) via Alternative Route EXAMPLE 1(ii) (a)

2-Hydroxymethylene-indan-1-one (Intermediate Leading to Compound 2)

1-Indanone (Aldrich) (5.0 g, 37.8 mmol) in toluene (25 cm$^3$) was added dropwise, to a stirring solution of sodium hydride (Aldrich) (1.8 g, 45.4 mmol 60% w/w dispersion in oil), ethyl formate (Aldrich) (5.6 g, 75.6 mmol) and toluene (50 cm$^3$), under nitrogen, at 0° C. The reaction was stirred for 17 hours before adding water (50 cm$^3$). The organic layer was washed with water and 2M NaOH. The combined aqueous extracts were acidified with 10 M HCl and the precipitate extracted with dichloromethane. The combined organic extracts were dried (Na$_2$SO$_4$), filtered and concentrated in vacuo to afford a yellow-orange solid. An analytically pure sample was obtained by Kugelrohr distillation (0.01 mmHg/100° C.) to give a yellow solid m.p. 110–112° C.

Found C, 74.9; H, 4.9% Calc. for C$_{10}$H$_8$O$_2$: C, 75.0; H, 5.0% $\delta_H$ (270 MHz, CDCl$_3$) 3.62 (2H, s, CH$_2$-3), 7.31–7.65 (3H, m, aryl), 7.66 (1H, s, CH$_2$-2), 7.84 (1H, d, J 7.8 Hz, Ar-H-7), 11.71 (1H, br s, OH). νmax (NUJOL)/cm$^{-1}$: 3050 (Ar—H str), 2621 (Aliph-H str and enol of 1, 2-dicarbonyl), 1694, 1682, 1621, 1614, 1567, 1574, 1556, 1531, 1519, 1538, 1504 (C=O str and C=C str).

EXAMPLE 1(ii) (b)

1-Phenyl-1, 4-dihydro-indeno[1,2-c] pyrazole (Intermediate Leading to Compound 2)

2-Hydroxymethlene indan-1-one (Example 1(ii)(a) (6.0 g, 37.5 mmol), phenylhydrazine hydrochloride (Aldrich) (5.48 g, 37.9 mmol), 10 M hydrochloric acid (1 cm$^3$) and ethanol (30 cm$^3$) were stirred under reflux for 19 hours. After cooling, the solvent was evaporated under reduced pressure and the residue dissolved in dichloromethane, then washed with 2M sodium hydroxide. The organic layer was separated, dried (Na$_2$SO$_4$) filtered and concentrated in vacuo. Purification by Kugelrohr distillation afforded an off-white solid (150° C., 0.01 mmHg) m.p. 119–120° C.

Found : C, 82.5; H, 5.1; N, 12.0% C$_{16}$H$_{12}$N$_2$ requires : C, 82.7; H, 5.2; N, 12.1% $\delta_H$ (250 MHz, CDCl$_3$) 3.67 (2H, s, 4-H), 7.25–7.80 (9H, m, aryl), 7.68 (1H, s, CH-3). νmax (NUJOL)/cm$^{-1}$: 3104, 3059 (Ar—H str), 2799, 2724, 2676, 2619 (Al—H str).

EXAMPLE 1(ii)(c)

1-Phenylamino-2-cyano-1-indene (Intermediate Leading to Compound 2)

1-Phenyl-1, 4-dihydro-indeno [1, 2-c) pyrazole (Example 1(ii)(b) (5.95 g, 25.6 mmol) sodium hydride (4.096 g, 102.4 mmol; 60% w/w dispersion in oil) and O-xylene (20 cm$^3$) were heated under reflux under nitrogen for 3 hours. After cooling, water was added and the mixture made neutral by the addition of hydrochloric acid. All organic matter was extracted with dichloromethane, then dried (Na$_2$SO$_4$), filtered and concentrated in vacuo. Purification was by column chromatography [Eluant: dichloromethane: ethanol (100:5)] followed by Kugelrohr distillation (155° C.; 0.01 mmHg) afforded an off-white solid, m.p. 151–153° C.

Found : C, 82.5; H, 5.2; N, 12.15% C$_{16}$H$_{12}$N$_2$ requires : C, 82.7; H, 5.2; N. 12.1% $\delta_H$ (250 MHz, CDCl$_3$) 3.68 (2H, s, 3-H), 6.69 (1H, br s, NH), 7.18–7.51 (9H, m, aryl). vmax (NUJOL)/cm$^{-1}$: 3300 (N—H str), 3128, 3061, 3042 (Ar—H str), 2177 (C≡N str), 1615, 1596, 1573, 1538 (C=C str).

EXAMPLE 1(ii)(d)

6-Amino-4,5-benzo-[5H]-cyclopenta-[1, 2b]-quinoline (Compound 2)

Under nitrogen, titanium tetrachloride (6.3 g, 3.7 cm$^3$, 33.15 mmol) was added to 1-phenylamino-2-cyano-1-indene (Example 1(ii) (c) (7.0 g; 30.14 mmol) and stirred at 140–150° C. for 1½ hours. After cooling, 10M NaOH (15 cm$^3$) was added and the whole was heated under reflux for 1½ hours. The cooled reaction mixture was then filtered and the residue washed with dichloromethane. The solid residue was further extracted using soxhlet apparatus (ethanol). The combined organic extracts were concentrated in vacuo to afford a dark solid. Purification by was column chromatography [Eluant: dichloromethane: ethanol: NH$_3$ (150:8:1)] followed by Kugelrohr distillation (220° C.; 0.05 mmHg) afforded an off-white solid, m.p. 250° (dec.)

Found : C, 82.5; H, 5.4; N, 12.3% C$_{16}$H$_{12}$N$_2$ requires : C, 82.7; H, 5.2; N, 12.1% $\delta_H$ [250 MHz, (CD$_3$)$_2$SO] 3.86 (2H, s, CH,), 7.09 (2H, br s, NH$_2$), 7.41–7.50 (3H, m, aryl), 7.64–7.68 (2H, m, aryl), 7.93 (1H, dd, J 1.0, 8.5 Hz, aryl) 8.09 (1H, m, aryl) 8.29 (1H, dd, J 1.0 & 8.4 Hz, aryl). vmax (NUJOL)/cm$^{-1}$: 3446, 3306 (N—H str), 3138, 3060, 3026 (Ar—H str), 1653, 1618, 1606, 1579, 1567, 1508 (C=C str).

EXAMPLE 1(ii) (e)

1-(4-Fluorophenyl)-1, 4-dihydro-indeno [1, 2-c] pyrazole (Intermediate Leading to Compound 34)

2-Hydroxymethylene indan-1-one, (Example 1(ii) (a) (4.004 g; 250 mmol), p-fluorophenyl hydrazine hydrochloride (Aldrich) (4.106 g; 25.25 mmol) 10M hydrochloric acid (1 cm$^3$) and ethanol (30 cm$^3$), were heated under reflux for 19 hours. After cooling, the solvent was evaporated under reduced pressure, then taken up in dichloromethane and washed with 2M NaOH. The organic layer was separated, dried (Na$_2$SO$_4$), filtered and concentrated in vacuo. Purification by Kugelrohr distillation (140° C.; 0.01 mmHg) afforded a yellow solid, m.p. 104–105° C.

Found : C, 76.5; H, 4.5; N, 11.3% M$^+$, 250.0880 C$_{16}$H$_{11}$FN$_2$ requires : C, 76.8; H, 4.4; N, 11.2% M, 250.096 $\delta_H$ (250 MHz, CDCl$_3$) 3.65 (2H, s, 4-H), 7.20–7.31 (4H, m, aryl), 7.44 (1H, m, aryl), 7.53 (1H, m, aryl), 7.65 (1H, s, 3-H), 7.66–7.72 (2H, m, aryl). vmax (NUJOL)/cm$^{-1}$: 3113, 3088, 3058, 3004 (Ar—H str), 1539, 1515 (C=C str), 1215 (C—F str).

EXAMPLE 1(ii)(f)

1-(4-Fluorophenyl)-2-cyano-1-indene (Intermediate Leading to Compound 34)

1-(4-Fluorophenyl)-1, 4-dihydro-indeno [1, 2-c] pyrazole (Example 1(ii) (e) (4.0 g; 15.98 mmol) sodium hydride (2.56 g; 63.92 mmol; 60% w.w dispersion in oil) and O-xylene (15 cm$^3$) were heated under reflux, under nitrogen, for 3 hours. After cooling, water was added and the mixture made neutral by the addition of hydrochloric acid. All organic material was extracted with dichloromethane and the combined extracts dried (Na$_2$SO$_4$) filtered and concentrated in vacuo. Purification was by column chromatography (Eluant: dichloromethane] gave the product and starting material, m.p. 172° C. (dec.) b.p. 155° C./0.01 mmHg.

Found : C, 76.5; H, 4.5; N, 11.2%; M$^+$, 250.0889 C$_{16}$H$_{11}$FN$_2$ requires : C, 76.8; H, 4.4; N, 11.2%; M, 250.0906. $\delta_H$ [250 MHz, (CD$_3$)$_2$SO] 3.65 (2H, s, CH$_2$-3), 7.15–7.35 (4H, m, aryl), 7.40–7.55 (3H, m, aryl), 7.88 (1H, m, aryl), 9.22 (1H, br S, NH). vmax (NUJOL)/cm$^{-1}$: 3340, 3302 (N—H str), 3142, 3078, 3064 (Ar—H str), 2179 (C≡N str), 1218 (C—F str).

EXAMPLE 1(ii)(g)

6-Amino-8-Fluoro-4, 5-benzo-[5H]-cyclopenta-[1, 2-b]-quinoline (34)

Under nitrogen to 1- (4-fluorophenyl) -2-cyano-1-indene (Example 1(ii)(f)) (1.0 g; 4.0 mmol) was added titanium tetrachloride (0.83 g; 0.48 cm$^3$; 4.4 mmol). The reaction mixture was then stirred at 140–150° C. for 1½ hours before cooling and adding 10 M NaOH (10 cm$^3$), then heating under reflux for a further 1 hour. The cooled reaction mixture was filtered and the residue washed with dichloromethane. The solid residue was further extracted using soxhlet apparatus for 17 hours (ethanol). The combined organic extracts were dried (Na$_2$SO$_4$), filtered and concentrated in vacuo to afford a dark solid. Purification was by column chromatography [Eluant: Dichloromethane: Ethanol: ammonia (100:8:1)] followed by Kugelrohr distillation (220° C.; 0.02 mmHg) gave the title compound, m.p. 250° C. (dec.).

Found : C, 76.55; H, 4.4; N, 11.4%; M$^+$, 250.0904 C$_{16}$H$_{11}$FN$_2$ requires : C, 76.8; H, 4.4; N, 11.2%; M, 250.0906 $\delta_H$ [(250 MHz, (CD$_3$)$_2$SO] 3.84 (2H, s, CH$_2$), 6.81 (2H, br s, NH$_2$), 7.43–7.54 (3H, m, aryl), 7.65 (1H, m, aryl), 7.95 (1H, dd, J 5.8 9.2 Hz, aryl), 8.01 (1H, m, aryl), 8.08 (1H, dd, J 2.8, 11.0 Hz, aryl). vmax (NUJOL)/cm$^{-1}$: 3484, 3316, 3270 (N—H str), 3185 (Ar—H str), 1190 (C—F str).

EXAMPLE 1(ii)(h)

1-(4'-Chlorophenyl)-1, 4-dihydro-indeno [1, 2-c] pyrazole (Intermediate Leading to Compound 35)

2-Hydroxymethyl inden-1-one (Example 1(ii)(a) (4.0 g; 25.00 mmol), p-chlorophenylhydrazine hydrochloride (Aldrich) (4.52 g; 25.25 mmol), 10M hydrochloric acid (1 cm$^3$) and ethanol (30 cm$^3$) were heated under reflux for 22 hours. After cooling, the solvent was evaporated and the residual dissolved in dichloromethane and washed with 2M sodium hydroxide. The organic extracts were then dried (Na$_2$SO$_4$), filtered and concentrated in vacuo. Purification was by column chromatography (Eluant: dichloromethane] and recrystallisation (ethanol) gave off-white needle shaped crystals, m.p. 128–129° C.; b.p. 185° C.; 0.05 mmHg.

Found : C, 72.2; H, 4.0; Cl, 13.7; N, 10.2% M$^+$ 268.0587, 266.0562 C$_{16}$H$_{11}$ClN$_2$ requires : C, 72.05; H, 4.2; Cl, 13.3; N, 10.5% M 268.0581, 266.0611 $\delta_H$ (250 MHz, CDCl$_3$) 3.66 (2H, s, 4-H), 7.25–7.46 (2H, m, aryl), 7.47–7.67 (4H, m, aryl), 7.69–7.72 (3H, m, aryl & 3-H). vmax (NUJOL)/cm$^{-1}$: 3110, 3085, 3054, 3044 (Ar—H str), 1533, 1506, 1487 (C=C str), 759 (C—Cl str).

EXAMPLE 1(ii)(i)

1(4-Chlorophenyl)-2-cyano-1-indene (Intermediate Leading to Compound 35)

Under nitrogen 1-(4'-chlorophenyl)-1, 4-dihydro-indeno [1, 2-c] pyrazole (Example 1(ii) (h) (3.0 g, 11.2 mmol), sodium hydride (1.80 g; 45 mmol; 60% dispersion in oil) and O-xylene (10 cm$^3$) and oxylene, were heated under reflux for 16 hours). After cooling, water was added and the mixture made neutral by the addition of hydrochloric acid. All organic material was extracted with dichloromethane then dried ($Na_2SO_4$), filtered and concentrated in vacuo to afford a dark solid. Purification was by column chromatography (Eluant: dichloromethane) and Kugelrohr distillation [210° C.; 0.05 mmHg] produced the product, m.p. 125–126° C.

Found : C, 72.0; H, 4.0; N, 10.3%; M+, 268.0600, 266.0508 $C_{16}H_{11}ClN_2$ requires : C, 72.05; H, 4.2; N, 10.5%; M, 268.0581, 266.0611 $\delta_H$ [(250 MHz, $(CD_3)SO$] 3.70 (2H, s, 4-H), 7.23–7.26 (2H, m, aryl), 7.28–7.57 (5H, m, aryl), 7.83–7.95 (1H, m, aryl), 9.33 (1H, br s, NH). vmax (NUJOL)/$cm^{-1}$: 3306 (N—H str), 3191, 3110, 3044 (Ar—H str), 2185 (C≡N str), 759 (C—Cl str).

EXAMPLE 1(ii)(j)

6-Amino-8-chloro-4, 5-benzo-[5H]-cyclopenta-[1,2-b]-quinoline (35)

Under nitrogen, titanium tetrachloride (0.65 g; 0.38 $cm^3$; 3.44 mmol), was added to 1-(4'-chlorophenyl) -2-cyano-1-indene (Example 1(ii)(i) (0.835 g; 3.13 mmol) and heated under reflux for 1½ hours. After cooling, 10M NaOH (10 $cm^3$) was added and heated under reflux for 1½ hours. After cooling the reaction was filtered and the residue washed with dichloromethane. The solid residue was further extracted using soxhlet apparatus (ethanol). The combined organic extracts were concentrated in vacuo to afford a dark solid. Purification was by column chromatography [Eluant: dichloromethane: ethanol: ammonia (200:8:1) and Kugelrohr distillation (250° C.; 0.05 mmHg) gave a brown solid, m.p. 247–249° C. (decomp.).

Found : C, 72.0; H, 4.2; Cl, 13.4; N, 10.55% M+, 268.0605, 266.0639 $C_{16}H_{11}ClN_2$ requires: C, 72.05; H, 4.2; Cl, 13.3; N, 10.5% M, 268.0581, 266.0611 $\delta_H$ [(250 MHz, $(CD_3)2SO$] 3.84 (2H, s, $CH_2$), 6.92 (2H, br s, $NH_2$), 7.42–7.51 (2H, m, aryl), 7.59 (1H, dd, J 2.3, 9.0 Hz, aryl), 7.63–770 (1H, m, aryl), 7.89 (1H, d, J 9.0 Hz, aryl), 7.97–8.04 (1H, m, aryl), 8.39 (1H, d, J 2.3, Hz, aryl). vmax (NUJOL)/$cm^{-1}$: 3457, 3308 (N—H str), 3194, 3059, 3011 (Ar—H str), 761 (C—Cl str).

EXAMPLE 1(ii)(k)

1-(4'-Methoxyphenyl)-1,4-dihydro-indeno[1,2-c] pyrazole (Intermediate Leading to Compound 36)

2-Hydroxymethylene inden-l-one (Example 1(ii) (a) (4.0 g; 25 mmol), p-methoxyphenyl hydrazine hydrochloride (Aldrich) (4.41 g; 25.25 mmol), 10 M hydrochloric acid (1 $cm^3$) and ethanol (30 $cm^3$), were heated under reflux, for 21 hours. After cooling, the mixture was concentrated in vacuo and the residue dissolved in dichloromethane, then washed with 2M NaOH, dried, filtered and concentrated in vacuo. Purification by column chromatography [Eluant: (dichloromethane: ethanol: ammonia (200:8:1)] Kugelrohr distillation (170° C.; 0.02 mmHg) and recrystallisation (ethanol) afforded needle shaped crystals, m.p. 102–103° C.

Found: C, 77.60; H, 5.5; N, 10.9%; M+, 262.1062 $C_{17}H_{14}N_2O$ requires : C, 77.8; H, 5.4; N, 10.7%; M, 262.1106 $\delta_H$ (250 MHz, $CDCl_3$) 3.65 (2H, s, 4-H), 3.90 (3H, s, O—$CH_3$), 7.04–7.10 (2H, m, aryl), 7.23–7.30 (2H, m, aryl), 7.45 (1H, m, aryl), 7.53 (1H, m, aryl), 7.60–7.66 (3H, m, aryl & 3-H). vmax (NUJOL)/$cm^{-1}$: 3107, 3072, 3049, 3005 (Ar—H str), 1537, 1518, 1498 (C=C str).

EXAMPLE 1(ii) (l)

1-(4'-Methoxyphenyl)-2-cyano-1-indene (Intermediate Leading to Compound 36)

Under nitrogen, 1-(4'-methoxyphenyl)-1, 4-dihydro-indeno [1, 2-c] pyrazole (Example 1(ii)(k) (3.0 g; 11.44 mmol), sodium hydride (Aldrich) (1.1 g; 27.5 mmol; 60% dispersed in oil) and o-xylene (10 $cm^3$), were heated under reflux for 16 hours. After cooling, water was added and the mixture made neutral by the addition of 2M HCl. All organics were extracted with dichloromethane, then dried ($Na_2SO_4$), filtered and concentrated in vacuo to afford a dark solid. Purification was by column chromatography [Eluant: dichloromethane: ethanol: ammonia (150:8:1)], followed by Kugelrohr distillation (205° C.; 0.05 mmHg) gave a colourless crystalline solid, m.p. 178–180° C.

Found : C, 77.8; H, 5.6; N, 10.8%, M+, 262.1132 $C_{17}H_{14}N_2O$ requires : C, 77.8; H, 5.4; N, 10.7%, M, 262.1106 $\delta_H$ (250 MHz, $CDCl_3$) 3.65 (2H, s, $CH_2$-3), 3.84 (3H, s, O—$CH_3$), 6.52 (1H, br s, NH), 6.93 (2H, d, J 8.8 Hz, Ar-H-2' & H-6'), 7.21 (2H, d, J 8.8 Hz, Ar—H-3' & H-5'), 7.30 (1H, d, J 7.0 Hz, aryl), 7.37 (1H, dd, J 1.1 & 8.9 Hz, aryl), 7.43 (1H, dd, J 1.0, 7.0 Hz, aryl), 7.48 (1H, d, J 7.3 Hz, aryl). vmax (NUJOL)/$cm^{-1}$: 3377 (N—H str), 3100, 3074, 3039 (Ar—H str), 2186 (C≡N str).

EXAMPLE 1(ii)(m)

6-Amino-8-methoxy-4,5-benzo-[5H]-cyclopenta-[1,2-b]-quinoline (36)

Under nitrogen, titanium tetrachloride (0.80 g; 0.46 $cm^3$; 4.2 mmol) was added to 1-(4'-methoxyphenyl)-2-cyano-1-indene (Example 1(ii)(1)) (1.0 g; 3.81 mmol) and heated under reflux for 3 hours. After cooling, 10M NaOH (15 $cm^3$) was added and heated under reflux for 1 hour. After cooling, the reaction was filtered and the residue washed with dichloromethane. The solid residue was further extracted using soxhlet apparatus (ethanol). The combined organic extracts were concentrated in vacuo and purified by column chromatography [Eluant: dichloromethane: ethanol: ammonia (100:8:1)] and Kugelrohr distillation (250° C.; 0.05 mmHg) to give a yellow solid, m.p. 234° C. (decomp.).

Found : C, 78.0; H, 5.3; N, 10.6%; M+, 262.1102 $C_{17}H_{14}N_2O$ requires : C, 77.8; H, 5.4; N, 10.7%; M, 262.1106 $\delta_H$ [(250 MHz, $(CD_3)$,SO] 3.83 (2H, s, 5-H), 3.90 (3H, s, O—$CH_3$, 7.26 (1H, dd, J 2.7, 9.1 Hz, 9-H), 7.39–7.47 (2H, m, 2-H & 3-H), 7.62–7.66 (2H, m & d, J 2.6 Hz, aryl & 7-H), 7.82 (1H, d, J 9.1 Hz, 10-H), 7.95–8.02 (1H, m, aryl). vmax (NUJOL)/$cm^{-1}$: 3426, 3325, 3273 (N—H str), 3163, 3051 (Ar—H str), 1660, 1608, 1563, 1521 (C=C str).

Examples Section 2: Illustration of the Synthesis of Compounds of Formula III and Pharmacological Activity Thereof

EXAMPLE 9(A)

Ethyl 1-Anilino-1-cyclopentene-2-carboxylate

A mixture of aniline (6.0 g, 64.5 mmol), ethyl cyclopentanone-2-carboxylate (Aldrich Chemicals) (10.0 g, 64.1 mmol) and calcium chloride (7.6 g, 68.5 mmol) in THF (100 ml) was heated under reflux for 24 hours. After being allowed to cool, the suspension was filtered and the solvent was removed from the filtrate under reduced pressure. Kugelrohr distillation of the residue (125° C., 0.02 mmHg) gave the title product as a pale yellow liquid.

(Found: C, 72.5; H, 7.4; N, 5.95, Calc. for $C_{14}H_{17}NO_2$: C, 72.7; H, 7.4; N, 6.1%. δH (250 MHz; $CDCl_3$) 1.32 (3H, t, J=7.1, $CH_3CH_2O$), 1.87, (2H, quin, J=7.4, $CH_2CH_2CH_2$), 5.28 (2H, t, J=7.2, $CH_2CCO_2R$), 2.80 (2H, t, J=7.5, C$H_2$CNHPh), 4.22 (2H, q, J=7.1, $CH_3CH_2O$), 7.00 –7.35 (5H, m Ar—H), 9.64 (1H, Br s, N$H$) m/z 231 (M+-7Et, 17%)

EXAMPLE 9(B)

12-Oxo-2,3,5,12-tetrahydro-β-quinindene

The above ester (Example 9(A)) (8.0 g, 34.6 mmol) was added dropwise to vigorously boiling biphenyl (32.0 g) and the mixture was left heating under reflux for 15 minutes and then allowed to cool. The biphenyl was removed by washing with dichloromethane and the resulting slurry filtered to give an off-white powder. Subsequent recrystallisation from ethanol gave the title compound as off-white crystals.

(Found: C, 77.8; H, 5.8; N, 7.4. Calc. for $C_{12}H_{17}NO$: C, 77.8; H, 6.0; N, 7.6%. δH[250 MHz, $(CH_3)_2SO$] 2.03 (2H, quin, J=7 .5, $CH_2C\underline{H}CH_2$), 2.69 (2H, t, J=7.3, $C\underline{H}_2CCO$), 2.98 (2H, t, J=7.8, $C\underline{H}_2CNH$), 7.26 (1H, tt, J=6.8 and 1.2, 8 or 9 Ar—$\underline{H}$). 7.47 (1H, d, J=7.6, 7 or 10 Ar—$\underline{H}$), 7.58 (1H, tt, J=6.8 and 1.5, 8 or 9 Ar—$\underline{H}$), 8.08 (1H, dd, J=8.1 and 1.3, 7 or 10 Ar-$\underline{H}$), 11.91 (1H, br s, N—$\underline{H}$).

EXAMPLE 9(C)

9-Chloro-2,3-dihydro-1H-cyclopenta [1,2-b] quinoline

The above quinoline (Example 9(B)) (3.6 g, 19.5 mmol) was heated under reflux with phosphorous oxychloride (20 ml, 215 mmol) for 1.5 hours. This was poured on to ice and gradually made alkaline with ammonia.

The precipitated solids were filtered and washed with copious amounts of water. The remaining solids were purified by Kugelrohr distillation (75° C., 0.1 mmHg) to give the title compound as a white powder.

(Found: C, 70.7; H, 5.0; N, 6.7; Cl, 17.5. Calc. for $C_{12}H_{10}ClN$: C, 70.8; H, 4.95; N, 6.9; Cl, 17.4%). δH (250 MHz); $CDCl_3$) 2.24 (2H quin, J=7.6, $CH_2C\underline{H}_2CH_2$), 3.16 (2H, t, J=7.5, $C\underline{H}_2CH_2CH_2$), 3.24 (2H, t, J=7.7, C $\underline{H}_2CH2CH_2$), 7.57 (1H, td, J=6.9 and 1.3, 8 or 9 Ar—H), 7.68 (1H, td, J=6.9, and 1.5, 8 or 9 Ar—$\underline{H}$), 8.04 (1H, dd, J=8.4 and 0.7, 7 or 10 Ar—$\underline{H}$), 8.15 (1H, dd, J=8.3 and 1.3, 7 or 10 Ar$\underline{H}$).

EXAMPLE 9(D)

N-(Phenylmethyl)-9-amino-2,3-dihydro-1H-cyclopenta[1,2-b] quinoline (28)

Chloroquinoline derivative (Example 9(C)) (2.0 g, 9.8 mmol), benzylamine (1.2 g, 11.2 mmol) and phenol (4.0 g, 42.6 mmol) were heated at 180° C. for 3 hours. After cooling, 5M sodium hydroxide (50 cm³) was added and the organic components were extracted into dichloromethane, dried ($Na_2SO_4$), filtered and the solvent was evaporated. Any remaining volatiles were removed by distillation and the residue was dissolved in hot ethanol, decolorised (charcoal) and recrystallised to give an off-white powder.

m.p. 173–174° C. (Found: C, 82.95; H, 6.5; N. 10.2;. $C_{19}H_{18}N_2$ requires C, 83.2; H, 6.6; N, 10.2%). δH (250 MHz; $CDCl_3$) 2.08 (2H, quin. J=7.5, $C\underline{H}_2$-2), 3.04 (2H, t, J=7.8, $C\underline{H}_2$-1), 3.17 (2H, t, J=7.2, $C\underline{H}_2$-3) 4.80 (2H, d, J=6.1, $C\underline{H}_2Ph$), 5.02 (1H, br s, N$\underline{H}$), 7.27–7.40 (6H, m, Ph—$\underline{H}$ and Ar—$\underline{H}$-7), 7.57 (1H, ddd, J=8.3, 6.9 and 1.3, Ar—$\underline{H}$ 8), 7.94 (1H, dd, J=8.4 and 1.2, Ar—$\underline{H}$-5). M/Z 274.147 ($M^+$, 95%).

EXAMPLE 10

2-Amino-cyclopent-1-ene-carbonitrile. (Intermediate leading to (22))

1, 4-Dicyanobutane (Aldrich Chemicals) (21. 6 g, 0. 2 mmol) sodium hydride (60% oil dispersion; 8.0 g, 0.2 mmol) and T.H.F. (100 ml) were heated under reflux for 16 hours. After cooling to 0° C., water (100 ml) was added and the upper layer was separated, dried ($Na_2SO_4$), filtered and the solvent evaporated. Recrystallisation from hot (80° C.) toluene gave the product.

m.p. 14514 146° C. (Found: C, 6.6; H, 7.77; N, 26.05. calc. for $C_6H_8N_2$ C, 66.6; H, 7.5; N, 25.9%). δH[250 MHz, $(CD_3)_2SO$] 1.76 (1H, quin, J=7.4, $C\underline{H}_2$-4), 2.33 (1H, t, J=7.9, $C\underline{H}_2$-3), 2.37 (1H, t, J=7.1, $C\underline{H}_2$-5), 6.36 (1H, br s, $N\underline{H}_2$).

EXAMPLE 11

2-Oxo-cyclopentane-carbonitrile (Intermediate leading to (22))

Cyano-enamine (Example 10) (2.7 g, 25 mmol) and 1M-hydrochloric acid (30 ml) were stirred at room temperature for 4 hours. The solution was saturated with ammonium chloride and the organic components were extracted into dimethyl ether, dried ($Na_2SO_4$), filtered and the ether was evaporated. Kugelrohr distillation (100° C., 1 mmHg) gave the product as a colourless liquid. (Found: C, 65.3; H, 6.3; N, 12.7. calc. for $C_6H_7NO$ C, 66.0; H, 6.5; N, 6.5; N, 12.8%) max (liquid film) /$cm^{-1}$3004 and 2902 (C—H), 2264 (CN) and 1779 (C=O). δH (400 MHZ; $CDCl_3$) 1.81–2.47 (6H, m, $C\underline{H}_2$), 3.17 (1H, ddd, J=10.9, 8.5 and 0.6, $C\underline{H}$-1).

EXAMPLE 12

2-(2-Chlorophenyl-aminocyclopent-1-ene-carbonitrile (Intermediate leading to (22))

2-Chloroaniline (Aldrich Chemicals) (2.6 g, 20.4 mmol), 2-oxo-cyclopentane-carbonitrile (Example 11) (2.2 g, 20.2 mmol), calcium chloride (2.5 g, 22.5 mmol) and T.H.F. (30 nml) were heated under reflux for 16 hours. This mixture was filtered and the solvent evaporated. Kugelrohr distillation (150° C., 0.5 mmHg) of the residue gave a pale yellow oil which slowly crystallised over time.

m.p. 69–72° C. (Found: C, 65.7; H, 5.0; N, 12.6; Cl, 16.35. $C_{12}H_{11}ClN_2$ requires C, 65.9; H, 5.1; N, 12.8; Cl, 16.2%. δH (250 MHz: $CDCl_3$) 2.00 (2H, quin, J=7.4, $C\underline{H}$-4), 2.62 (2H, t, J=7.2, $C\underline{H}_2$-3) , 2.70 (2H, t, J=7.5, $C\underline{H}_2$-5), 6.69 (1H, br s, N$\underline{H}$), 7.03 (1H, ddd, J=8.4, 7.5 and 1.7, Ar—$\underline{H}$-4-) 7.21 (1H, ddd, J=8.1, 7.1 and 1.8, Ar—$\underline{H}$-5-) 7.22 (1H, dd, J=7.2 and 1.0, Ar—$\underline{H}$-6-), 7.39 (1H, dd, J=8.0 and 1.3, Ar—$\underline{H}$-3⁻).

EXAMPLE 13

9-Amino-5-chloro-2,3-dihydro-1H-cyclopenta[b] quinoline (22)

Substituted aniline (Example 12) (2.2 g, 10.0 mmol) and titanium tetrachloride (1.2 ml, 11.0 mmol) under a dry nitrogen atmosphere were heated together at 140° C. for 1 hour. After cooling, 10M-sodium hydroxide (20 ml) was added and the mixture was heated under reflux for 1 hour. Any organic components were extracted into dichloromethane dried ($Na_2SO_4$), filtered and the solvent evaporated. Kugelrohr distillation (225° C., 0.5 mmHg) gave the product as pale yellow crystals.

m.p. 249–250° C. (dec). (Found: C, 66.0; H, 5.3; N, 12.8; Cl, 156.4, $C_{12}H_{11}ClN_2$ requires C, 65.9; H, 5.1; N, 12.8; Cl, 16.2%). δH[250 MHz; $(CD_3)_2SO$] 2.08 (2H, quin, J=7.5, C $\underline{H}_2$-2), 2.82 (2H, t, J=7.3, $C\underline{H}_2$-1), 2.94 (2H, t, J=7.7, $C\underline{H}_2$-3), 6.62 (2H, s, $N\underline{H}_2$), 7.25 (1H, dd, J=8.4 and 7.6, Ar—$\underline{H}$-7), 7.67 (1H, dd, J=7.4 and 1.2, Ar—$\underline{H}$-8), 8.12 (1H, dd, J=8.4 and 1.2, Ar—$\underline{H}$-6).

EXAMPLE 14

2-(4-Chlorophenyl) amino-cyclopentene-1-carbonitrile (Intermediate of (19))

4-Chloro-aniline (Aldrich Chemicals) (2.6 g, 20 mmol), cyanoketone (Example 11) (2.2 g, 20 mmol), calcium chloride (2.5 g, 23 mmol) and T.H.F. (30 ml) were heated under reflux for 19 hours. After being allowed to cool, the mixture was filtered and the solvent evaporated. Kugelrohr distillation (160° C., 0.3 mm Hg) gave the product as white crystals.

m.P. 130–132° C. (Found: C, 65.9; H, 5.0; N, 12.7; Cl, 16.5; $C_{12}H_{11}ClN_2$ requires C, 65.9; H. 5.1; N, 12.8; Cl. 16.2%). δH (250 MHZ; $CDCl_3$) 1.97 (2H, quin, J=7.4, C$\underline{H}_2$-4), 2.59 (2H, tt, J=8.0, 1.3 C$\underline{H}_2$-3), 2.66 (2H, t, J=7.6, C$\underline{H}_2$-5), 6.80 (1H, br s, N$\underline{H}$), 6.96 (2H, dt, J=9.4, 2.6, Ar—$\underline{H}$-2',6'), 7.26 (2H, dt, J=9.4, 2.6. Ar—H-3', 5'). m/z 218.0597 ($M^+$, 100%), 220.0572 ($M^++2$, 36%).

EXAMPLE 15

9-Amino-7-chloro-2,3-dihydro-1H-cyclopenta-[b]quinoline (19)

Under nitrogen, titanium tetrachloride (1.2 ml, 11 mmol) was added to the above enamine (Example 14) (2.2 g, 10 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried ($Na_2SO_4$), filtered and the solvent evaporated, Kugelrohr distillation (200° C., 2 mm Hg) gave the product as a pale yellow powder.

m.p. 228–230° C. (dec). (Found: C, 65.8; H, 5.0; N, 12.7; Cl, 6.2. Calc. for $C_{12}H_{11}ClN_2$ C, 65.9; H, 5.1; N, 12.8; Cl, 16.2%). δH(250 MHz; $(CD_3)_2$ SO], 2.02 (2H, quin, J=7.4, C$\underline{H}_2$-2), 2.80 (2H, t, J=7.3, C$\underline{H}_2$-1), 2.89 (2H, t, J=7.7, C$\underline{H}_2$-3), 6.54 (2H, s, N$\underline{H}_2$), 7.48 (1H, dd, J=9.0, 2.3, Ar—$\underline{H}$-6), 7.67 (1H, d, J=8.9, Ar—$\underline{H}$-5), 8.26 (1H, d, J=2.2, Ar—$\underline{H}$-8).

EXAMPLE 16

2-(2'Fluorophenyl) amino-cyclopentene-1-carbonitrile (Intermediate leading to (13))

2-Fluoro-aniline (Aldrich Chemicals) (2.3 g, 21 mmol), cyanoketone (Example 11) (2.2 g, 20 mmol), calcium chloride (2.5 g, 23 mmol) and T.H.F. (30 ml) were heated under reflux for 24 hours. After being allowed to cool, the mixture was filtered and the solvent evaporated. Kugelrohr distillation (125° C. 0.05 mm Hg) have the product as an off-white power.

m.p. 91–92° C. (Found: C, 71.1; H, 5.5; N, 13.7. $C_{12}H_{11}FN_2$ requires C, 71.3; H, 5.5; N, 13.85%) δH (250 MHz; $CDCl_3$) 1.99 (2H, quin, J=7.3, C$\underline{H}_2$-4), 2.68 (2H, t, J=7.4, $CH_2$-3), 2.61 (2H, t, J=7.8, C$\underline{H}_2$-5), 6.44 (1H, Br s, N$\underline{H}$, 7.07–7.19 (4H, m, Ar—$\underline{H}$). δF (377 MHz; $CDCl_3$)-127.5 (s, Ar—$\underline{F}$-2').

EXAMPLE 17

9-Amino-5-fluoro-2,3-dihydro-1H-cyclopenta-[1,2-b]quinoline (13)

Under nitrogen, titanium tetrachloride (1.2 ml, 11 mmol) was added to the above enamine (Example 8) (2.0 g, 10 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried ($Na_2SO_4$), filtered and the solvent evaporated. Kugelrohr distillation (175° C., 0.04 mm Hg) gave the product as an off-white powder.

m.p. 257–260° C. (dec). (Found: C, 71.3; H, 5.3; N, 13.7, $C_{12}H_{11}FN_2$ requires C, 71.3; H, 5.5; N, 13.85%). δH [400 MHz; $(CD_3)_2SO$] 2.06 (2H, quin, J=7.5, C$\underline{H}_2$-2, 2.83 (2H, t, J=7.3, C$\underline{H}_2$-1), 2.92 (2H, t, J=7.7, C$\underline{H}_2$-3), 6.54 (2H, s, N$\underline{H}_2$), 7.24 (1H, td, J=7.9, 5.4, Ar—$\underline{H}$-7), 7.30 (1H, ddd, J=11.2, 7.6, 1.2, Ar—$\underline{H}$-8).

EXAMPLE 18

2-(3'-Fluorophenyl) amino-cyclopentene-1-carbonitrile (Intermediate leading to 15))

3-Fluoro-aniline (Aldrich Chemicals) (4.6 g, 41 mmol), cyano-ketone (Example 11) (4.4 g, 40 mmol), calcium chloride (5.0 g, 45 mmol) and T.H.F. (60 ml) were heated under reflux for 17 hours. After being allowed to cool, the mixture was filtered and the solvent evaporated. Kugelrohr distillation (125° C., 0.02 mm Hg) gave the product as a pale yellow powder.

m.p. 98–100° C. (Found: C, 71.25; H. 5.25; N, 14.0. $C_{12}H_{11}FN_2$ requires C, 71.3; H, 5.5; N, 13.85%). δH (250 MHz; $CDCl_3$) 1.99 (2H, quin, J=7.4, C$\underline{H}_2$-4), 2.59 (2H, tt, J=7.2, 1.4, $CH_2$-5), 2.73 (2H, t, J=7.5, C$\underline{H}_2$-3), 6.70–6.80 (3H, m, Ar—$\underline{H}$-4, 5 and 6), 6.96 (1H, br s, N$\underline{H}$), 7.20–7.30 (1H, m, Ar—$\underline{H}$-2). δF (377 MHz; $CDCl_3$) 111.9 (m, Ar—$\underline{F}$-3).

EXAMPLE 19

9-Amino-8-fluoro-2,3-dihydro-1H-cyclopenta-[b]quinoline (14) and 9-amino-6-fluoro-2,3-dihydro-1H-cyclopenta [b] quinoline (15)

Under nitrogen, titanium tetrachloride (2.4 ml, 22 mmol) was added to the above enamine (Example 18) (4.0 g, 20 mmol) and the stirred mixture was heated at 140° C. for 1 hour. After cooling, 10M-sodium hydroxide solution (40 ml) was added and the mixture heated under reflux for 1 hour. After being allowed to cool, this mixture was filtered and the solids washed with dichloromethane. Any organics in the filtrate were also extracted into dichloromethane. All extracts were combined, dried ($Na_2SO_4$), were filtered and the solvent evaporated. Kugelrohr distillation (150–175° C., 0.05 mm Hg) followed by chromatography on silica with chloroform-ethanol-10M ammonia solution (100:8:1) as the eluant gave two products. Kugelrohr distillation of the first fraction (170° C., 0.8 mm Hg) gave an off-white powder (14). A similar distillation of the second fraction (175° C., 0.7 mm Hg) gave a white powder (14).

m.p. 172–173° C. (14). (Found: C, 71.1; H, 5.7; N, 13.9. calc. for $C_{12}H_{11}FN_2$ C, 71.3; H, 5.5; N, 13.85%). δH[400 MHz; $(CD_3)_2SO$] 2.00 (2H, quin, J=7.5, C$\underline{H}_2$-3), 2.75 (2H, t, J=7.2, C$\underline{H}_2$-1), 2.84 (2H, t, J=7.78, C$\underline{H}_2$-3), 6.19 (2H, s, N$\underline{H}_2$), 6.98 (1H, ddd, J=13.8, 7.3, 1.4, Ar—$\underline{H}$-7), 7.37 (1H, td, J=8.0, 6.0, Ar—$\underline{H}$-6), 7.45 (1H, dd, 8.6, 1.4, Ar—$\underline{H}$-5). δF[377 MHz; $(CD_3)_2SO$] 144.4(m, Ar—$\underline{F}$-8). m.p. 235–236° C. (15). (Found: C, 71.4; H, 5.5; N, 13.8. $C_{12}H_{11}FN_2$ requires C, 71.3; C, 5.5; N, 13.85%). δH[400 MHz; $(CD_3)_2SO$] 2.05 (2H, quin, J=7.5, C$\underline{H}_2$-2), 2.80 (2H, t, J=7.3, CH$_2$-1), 2.89 (2H, t, J=7.7, CH$_2$-3), 6.52 (2H, s, NH$_2$), 7.19 (1H, td, J=8.7, 2.7, Ar—H-7), 7.34 (1H, dd, J=11.1, 2.7, Ar—H-5), 8.20 (1H, dd, J=9.2, 6.4, Ar—H-8). δF[377 MHz; (CD$_3$)$_2$SO] 113.8 (m, Ar—F-6).

EXAMPLE 20

2-(4'-Fluorophenyl) amino-cyclopentene-1-carbonitrile (Intermediate leading to (11))

4-Fluoro-aniline (Aldrich Chemicals) (2.3 g, 21 mmol), cyano-ketone (Example 11) (2.2 g, 20 mmol), calcium chloride (2.5 g, 23 mmol) and T.H.F. (30 ml) were heated under reflux for 21 hours. After being allowed to cool, the mixture was filtered and the solvent evaporated. Kugelrohr distillation (160° C., 0.4 mm Hg) gave the product as an off-white powder.

m.p. 100–102° C. (Found: C, 71.3; H, 5.5; N, 13.8, C$_{12}$H$_{11}$FN$_2$ requires C, 71.3; H, 5.5; N, 13.85%). δH (250 MHz; CDCl$_3$) 1.95 (2H, quin, J=7.4, CH$_2$-4), 2.58 (4H, t, J=7.4, CH$_2$-3 and 5), 6.66 (1H, br s, NH), 7.00 (2H, s, Ar—H-2' and 6'), 7.02 (2H, s, Ar—H-3' and 5'). δF (377 MHz; CDCl$_3$) 118.4(s, Ar—F-4').

EXAMPLE 21

9-Amino-7-fluoro-2,3-dihydro-1H-cyclopenta-[b]quinoline (11)

Under nitrogen, titanium tetrachloride (1.2 ml, 11 mmol) was added to the above enamine (Example 20) (2.0 g, 10 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried (Na$_2$SO$_4$), filtered and the solvent evaporated. Kugelrohr distillation (175° C., 0.05 mmHg) gave the product as an off-white powder.

m.p. 230–232° C. (dec). (Found: C, 71.0; H, 5.5; N, 13.9 C$_{12}$H$_{11}$FN$_2$ requires C, 71.3; H, 5.5; N, 13.85%). δH[250 MHz; (CD$_3$)$_2$SO] 2.05 (2H, quin, J=7.5, CH$_2$-2), 2.80 (2H, t, J=7.3, CH$_2$-1), 2.88 (2H, t, J=7.7, CH$_2$-3), 6.41 (2H, s, NH$_2$), 7.38 (1H, td, J=8.7, 2.8, Ar—H-6), 7.71, (1H, dd, J=9.2, 5.8, Ar—H-5), 7.93 (1H, dd, J=11.1, 2.8, Ar—H-8). δF[377 MHz: (CD$_3$)$_2$SO]-118.1 (s, Ar—F-7).

EXAMPLE 22

2-(4'Bromophenyl) amino-cyclopentene-1-carbonitrile (Intermediate leading to 25))

4-Bromo-aniline (Aldrich Chemicals) (3.5 g, 20 mmol), cyano-ketone (Example 11) (2.2 g, 20 mmol), calcium chloride (2.5 g, 23 mmol) and T.H.F. (30 ml) were heated under reflux for 7 hours. After being allowed to cool, the mixture was filtered and the solvent evaporated. Kugelrohr distillation (150° C., 0.07 mmHg) gave the product as a brown-grey powder.

m.p. 136–138° C. (Found: C, 55.0; H, 4.3; N, 10.8; Br, 30.6. calc. for C$_{12}$H$_{11}$BrN$_2$ C, 54.8; H, 4.2; N, 10.65; Br, 30.4%. δH (250 MHz, CDCl$_3$) 1.98 (2H, quin, J=7.4, CH$_2$-4), 2.59 (2H, tt, J=7.2, 1.5. CH$_2$-4), 2.67 (2H, t, J=7.5, CH$_2$-3), 6.68 (1H, br s, NH), 6.90 (2H, d, J=8.8, Ar—H-2' and 6'), 7.41 (2H, d, J=8.8, Ar—H-3' and 5').

EXAMPLE 23

9-Amino-7-bromo-2,3-dihydro-1H-cyclopenta-[1,2-b] quinoline (25)

Under nitrogen, titanium tetrachloride (1.2 ml, 11 mmol) was added to the above enamine (Example 22) (2.6 g, 20 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried (Na$_2$SO$_4$), filtered and the solvent evaporated. Kugelrohr distillation (180° C., 0.04 mmHg) gave the product as a pale yellow powder.

m.p. 236–238° C. (Found: C, 54.75; H. 4.1; N, 10.7; Br, 30.4/ C$_{12}$H$_{11}$BrN$_2$ requires C, 24.8; H, 4.2; N, 10.65; Br, 30.4%. δH[250 MHz; (CD$_3$)$_2$SO] 2.04 (2H, quin, J=7.5, CH$_2$-2), 2.80 (2H, t, J=7.3, CH$_2$-1), 2.88 (2H, t, J=7.7, CH$_2$-3), 6.55 (2H, s, NH$_2$), 7.60 (2H, s, Ar—H-5 and 6), 8.40 (1H, m, Ar—H-8).

EXAMPLE 24

2-(3'-Chlorophenyl)aminocyclopent-1-ene-carbonitrile. (Intermediate leading to (16) and (17))

3-Chloro-aniline (Aldrich Chemicals) (5.1 g, 40.0 mmol), cyano-ketone (Example 11) (4.4 g, 40.4 mmol) and calcium chloride (5.0 g, 45.0 mmol) in T.H.F. (60 ml) were heated under reflux for 17 hours. After cooling, the mixture was filtered and the solvent evaporated. Kugelrohr distillation (150° C., 0.2 mmHg) gave the product as light yellow powder.

m.p. 111–112° C. (Found: C, 65.9; H, 5.1; N, 12.6; Cl, 16.5. C$_{12}$H$_{11}$ClN$_2$ requires C, 65.9; H, 5.1; N, 12.8; Cl, 16.2%). δH (250 MHz; CDCl$_3$) 1.99 (2H, quin, J=7.4, CH$_2$-4), 2.60 (2H, tt, J=7.2, 1.5 CH$_2$-5), 2.72 (2H, t, J=7.5, CH$_2$-3), 6.77 (1H, br s, NH, 6.90) (1H, ddd, J=8.1, 2.1, 1.3, Ar—H-4'), 7.02 (1H, dd, J=2.0, 2.0, Ar—H-2'), (1H, ddd, J=9.8, 1.9, 1.0, Ar—H-6'), 7.23 (1H, dd, J=8.0, 8.0, Ar—H-5').

EXAMPLE 25

9-Amino-8-chloro-2,3-dihydro-1H-cyclopenta[b]quinoline and 9-amino-6-chloro-2,3-dihydro-1H-cyclopenta[b] quinoline (16) and (17)

Under nitrogen, titanium tetrachloride (2.4 ml, 22 mmol) was added to the above enamine (Example 24) (4.4 g, 20 mmol) and the stirred mixture was heated at 140° C. for 1 hour. After cooling, 10M-sodium hydroxide solution (40 ml) was added and the mixture heated reflux for 1 hour. After being allowed to cool, this mixture was filtered and the solids washed with dichloromethane. Any organics in the filtrate were also extracted into dichloromethane. All extractions were combined, dried (Na$_2$SO$_4$), filtered and the solvent evaporated. Kugelrohr distillation (175–200° C., 0.02 mmhg) followed by chromatography on silica with chloroform-ethanol-10M ammonia solution (200:8:1) as the eluent gave two products. Kugelrohr distillation of the first fraction (160° C., 0.08 mmHg) gave a white powder (16). A similar distillation of the second fraction (200° C., 0.03 mmHg) gave an off-white powder (17).

i) m.p. 185° (16)

(Found: C,65.95; H. 5.35; N, 12.8; Cl, 16.2. calc. for C$_{12}$H$_{11}$ClN$_2$; C, 65.9; H, 5.1; N, 12.8; Cl, 16.2%). δH [250 MHz; (CD$_3$)$_2$SO] 2.07 (2H, quin, J=7.6, CH$_2$-2), 2.79 (2H, t, J=7.3, CH$_2$-1), 2.91 (2H, t, J=7.7, CH$_2$-3), 6.53 (2H, br s, NH$_2$), 7.34 (1H, dd, J=7.5, 1.5. Ar—H-7), 7.42 (1H, t, J=7.8, Ar—H-6), 7.65 (1H, dd, J=8.2, 1.5, ArH-5)

ii) m.p. 271–272° C. (dec) (17)

(Found: C, 65.5; H, 4.9; N, 12.7; Cl, 17.4. C$_{12}$H$_{11}$ClN, requires C, 65.9; H, 5.1; N, 12.8; Cl, 16.2%). δH[250 MHz;

(CD$_3$)$_2$SO] 2.06 (2H, quin, J=7.5, CH$_2$-2), 2.80 (2H, t, J=7.3, CH$_2$-1), 2.91 (2H, t, J=7.7, CH$_2$-3), 6.77 (2H, br s, NH$_2$), 7.34 (1H, dd, J=8.9, 2.2, Ar—H-7), 7.68 (1H, d, J=2.2, Ar—H-5), 8.18 (1H, d, d=9.0, Ar—H-8).

EXAMPLE 26

2-(2',4'-Difluorophenyl)aminocyclopent-1-ene-1-carbonitrile (Intermediate leading to 32)

2,4-Difluoro-aniline (2.6 g, 20.0 mmol) (Aldrich Chemicals) cyano-ketone (Example 11) (2.2 g, 20.2 mmol), calcium chloride (2.5 g, 22.5 mmol) and T.H.F. (30 ml) were heated under reflux for 19 hours. After cooling, the mixture was filtered and the solvent evaporated. Kugelrohr distillation (125° C., 0.25 mmHg) gave the product as pale yellow crystals.

m.p. 116–119° C. (Found: C, 65.3; H, 4.9; N, 12.4. C$_{12}$H$_{10}$F$_1$N$_2$ requires C, 65.54; H, 4.6; N, 12.7%. δH (400 MHz; CDCl$_3$) 1.96 (2H, quin, J=7.4, CH$_2$-4), 2.56 (2H, tt, J=7.8, 2.4, CH$_2$-5), 2.60 (2H, tt, J=7.2, 1.5, CH$_2$-3), 6.26 (1H, Br s, NH), 6.85 (1H, td, J=8.3, 2.7, Ar—H-3'), 6.88 (1H, dddd, J=9.1, 7.9, 2.8, 1.5, Ar—H-5') 7.15 (1H, td, J=9.0, 5.7, ArH-6'). δF (377 MHz; CDCl$_3$) 113.49 (1F, tt, J=8.1, 5.7, Ar—F-4'), 121.09 (1F, td, J=9.5, 5.7, Ar—F-2').

EXAMPLE 27

9-Amino-5,7-difluoro-2.3dihydro-1H-cyclopenta[1,2b]quinoline (32)

Under nitrogen, titanium tetrachloride (1.2 ml, 11 mmol) was added to the above enamine (Example 26) (2.2 g, 10 mmol) and the stirred mixture was heated at 140° C. for 1 hour. After cooling, 10M-sodium hydroxide (20 ml) was added and the mixture heated under reflux for 1 hour. After being allowed to cool, this mixture was filtered and the solid washed with dichloromethane. Any organics in the filtrate were also extracted into dichloromethane. All extracts were combined, dried (Na$_2$SO$_4$), filtered and the solvent evaporated. Kugelrohr distillation (175° C., 0.08 mmHg) gave the product as a yellow powder.

m.p. 250° C. (dec) (Found: C, 65.7; H, 4.8; N, 12.7. C$_{12}$H$_{10}$F$_2$N$_2$ requires C, 65.45; H, 4.6; N, 12.7%). δH[400 MHz; (CD$_3$)$_2$SO] 2.07 (2H, quin, J=7.5, CH$_2$-2), 2.82 (2H, t, J=7.3, CH$_2$-1), 2.91 (2H, t, J=7.7, CH$_2$-3), 6.54 (2H, s, N H$_2$), 7.40 (1H, ddd, J=11.3, 8.8, 2.6, Ar—H-6), 7.81 (1H, ddd, J=10.9, 2.5, 1.6. Ar—H-8). δF[377 MHz; (CD$_3$)$_2$SO]-115.96 (1F, ddd, J=10.7, 9.0, 5.7, Ar—F-7) 120.10 (1F, ddd, J=11.1, 5.8, 1.4, Ar—F-5).

EXAMPLE 28

2-(2'5'-Difluorophenyl) aminocyclopent-1-ene-1-carbonitrile (Intermediate leading to 31)

2,5-Difluoro-aniline (2.6 g, 20.0 mmol) (Aldrich Chemicals) cyano-ketone (Example 11) (2.2 g, 20.2 mmol), calcium chloride (2.5 g, 22.5 mmol) and T.H.F. (30 ml) were heated under reflux for 22 hours. After cooling, the mixture was filtered and the solvent evaporated. Kugelrohr distillation (160° C., 0.9 mmHg) gave the produce as white crystals.

m.p. 102–103° C. (Found: C, 65.7; H, 4.75; N. 12.75. C$_{12}$H$_{10}$F$_2$N$_2$ requires C, 65.45; H, 4.6; N, 12.7%) δH (400 MHz; CDCl$_3$) 2.04 (2H, quin, J=7.4, CH$_2$-4), 2.63 (2H, tt, J=7.3, 1.6, CH$_2$-5), 2.75 (2H, t, J=7.6, CH$_2$-2), 6.51 (1H, Br s, NH), 6.72 (1H, ddt, J=9.0, 7.5, 3.3, Ar—H-4'), 6.86 (1H, ddd, J=9.5, 6.6, 3.0, Ar—H-6'), 7.06 (1H, ddd, J=10.0, 9.1, 5.0, Ar—H-3'). δF (377 MHz; CDCl$_3$) 116.94 (1F, dddd, J=1.0, 7.1, 3.6, 0.8, Ar—F-5'), 134.79 (IF, dddd, J=10.2, 6.4, 3.8, 2.7, Ar—F-2').

EXAMPLE 29

9-Amino-5,8-difluoro-2,3-dihydro-1H-cyclopenta [1.2b] quinoline (31)

Under nitrogen, titanium tetrachloride (0.9 ml, 8.2 mmol) was added to the above enamine (Example 28) ( 1.65 G, 7.5 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried (Na$_2$SO$_4$), filtered and the solvent evaporated. Kugelrohr distillation (170° C., 0.06 mmHg) gave the product as a yellow powder.

m.p. 168–171° C. (Found: C, 65.3; H, 4.6; N, 12.8. C$_{12}$H$_{10}$F$_2$N$_2$ requires C, 65.45; H, 4.6; N, 12.7%). δH[400 MHz; (CD$_3$)$_2$SO] 2.07 (2H, quin, J=7.6, CH$_2$-2), 2.82 (2H, t, J=7.4, CH$_2$-1), 2.93 (2H, t, J=7.7, CH$_2$-3), 6.39 (2H, s, NH$_2$), 7.01 (1H, ddd, J=12.8, 8.6, 4.1. Ar—H-7), 7.28 (1H , ddd, J-10.6, 8.7, 4.6, Ar—H-6). δH[377 MHz; (CD$_3$)$_2$SO]-128.18 (1F, dd, J=10..5, 3.9. Ar—F-8), 128.23 (1F, dd, J=10.6, 4.0, Ar-F-5).

EXAMPLE 30

2-(3', 4'-Difluorophenyl) aminocyclopent-1-ene-1-carbonitrile. (Intermediate leading to (10) and (8))

3,4'Difluoro-aniline (Avocado) (5.0 g, 38.8 mmol), cyano-ketone (Example 11) (4.3 g, 39.4 mmol), calcium chloride (4.5 g, 40.5 mmol) and T.H.F. (60 ml) were heated under reflux for 18 hours. After cooling, the mixture was filtered and the solvent evaporated. Kugelrohr distillation (150° C., 0.1 mmHg) gave the product as a pale pink powder.

m.p. 126–128° C. (Found: C, 65.3; H, 4.7; N, 13.0. C$_{12}$H$_{11}$F$_2$N$_2$ requires C, 65.45; H, 4.6; N, 12.7%). δH (400 MHz: CDCl$_3$) 1.99 (2H, quin, J=7.4, CH$_2$-4), 2.60 (2H, tt, J=7.2, 1.5, CH$_2$-5), 2.64 (2H, tt, J=7.5, 1.4, CH$_2$-3), 6.57 (1H , br s, NH), 6.76 (1H , tdt, J-8.4, 4.0, 1.8, Ar—H-6'), 6.88 (1H , dd, J=11.3, 6.8, 2.7, Ar—H-2'), 7.11 (1H , dt, J=9.9, 8.8, Ar—H-5'). δF (377 MHz; CDCl$_3$)-135 (1F, dddd, J=21.6, 11.3, 8.7, 1.7, Ar—F-3').–143.21 (1F, dddd, J=21.5, 10.2, 6.8, 3.7, Ar—F-4').

EXAMPLE 31

2-Aminocyclohex-1-ene-1-carbonitrile (Intermediate leading to (18))

1,5-Dicyanopentane (Aldrich Chemicals) (25.0 g, 205 mmol), sodium hydride (60% oil dispersion; 8.2 g, 205 mmol) and T.H.F. (150 ml) were heated under reflux for 17 hours. After cooling, water (150 ml) was added and the upper organic layer removed, dried (Na$_2$SO$_4$) filtered and the solvent evaporated. Recrystallisation from hot toluene (80° C.) gave the product as beige crystals.

m.p. 90–92° C. (Found: c, 68.8; H, 8.5; N, 23.0. Calc. for C$_7$H$_{10}$N$_2$: C, 68.8; H, 8.25; N, 22.9%). δH[250 MHz; (CD$_3$)$_2$SO] 1.52 (4H, m, CH$_2$-4 and 5), 2.05 (2H, t, J=4.4, CH$_2$-3, 2.07 (2H, t, 4.4. CH$_2$-6), 5.80 (2H, br s, NH$_2$).

EXAMPLE 32

2-Oxocyclohexane-1-carbonitrile (Intermediate leading to (18))

The above cyano-enamine (Example 31) (16.0 g, 131 mmol) and 1M-hydrochloric acid (150 ml) were stirred at room temperature for 17 hours. The suspension was saturated with ammonium chloride and the organic components were extracted into diethyl ether, dried (Na$_2$SO$_4$), filtered and the ether was evaporated. Kugelrohr distillation (100° C., 0.2 mmHg) gave the product as a colourless liquid.

(Found: C, 68.6; H, 7.6; N, 11.5. Calc. for C$_7$H$_9$NO: C, 68.3; H, 7.4; N, 11.4%). $\delta_H$(250 MHz: CDCl$_3$ 1.58–2.54 (8H, m, CH$_2$), 3.54 (1H, dd, J=11.6, 5.5, CHCN).

EXAMPLE 33

2-(4'Fluorophenyl) aminocyclohex-1-ene-1-carbonitrile (Intermediate leading to (18))

4-Fluoro-aniline (1.11 g, 10.0 mmol), cyano-ketone (Example 32) (1.25 g, 10.2 mmol), calcium chloride (1.5 g, 13.5 mmol) and T.H.F. (20 ml) were heated under reflux for 17 hours. After cooling, the mixture was filtered and the solvent evaporated. Kugelrohr distillation (135° C., 0.08 mmHg) gave the product as a pale yellow powder.

m.p. 79–82° C. (Found: C, 72.0; H, 6.3; N, 13.1. C$_{13}$H$_{13}$FN$_2$ requires C, 72.2; H, 6.1; N, 12.95%). $\delta_H$ (400 MHz; CDCl$_3$) 1.64 (4H, m, CH$_2$-4 and 5), 2.15 (2H, m, CH$_2$-6), 2.29 (2H, m, CH$_2$-3), 6.37 (1H, br s, NH), 7.00 (2H, s, Ar—H-2' and 6'), 7.02 (2H, s, Ar—H-3' and 5'). $\delta_F$ (377 MHz; CDCl$_3$) 117.64 (1F quin, J=6.5, 0.8, Ar—F-4').

EXAMPLE 34

9-Amino-7-fluoro-1, 2, 3, 4-tetrahydro-acridine (18)

Under nitrogen, titanium tetrachloride (0.9 ml, 8.2 mmol) was added to the above enamine (Example 33) (1.5 g, 7.5 mmol) and the stirred mixture was heated at 140° C. for 1 hour. After cooling, 10M-sodium hydroxide solution (20 ml) was added and the mixture heated under reflux for 1 hour. After being allowed to cool, this mixture was filtered and the solids washed with dichloromethane. Any organics in the filtrate were also extracted into dichloromethane. All extracts were combined, dried (Na$_2$SO$_4$), filtered and the solvent evaporated. Kugelrohr distillation (175° C., 0.05 mmHg) gave the product as a pale yellow powder.

m.p. 229–230° C. (Found: C, 72.4; H, 6.15; N, 13.2. C$_{13}$H$_{13}$N$_2$F requires C, 72.2; H, 6.1; N, 12.95%). $\delta_H$ (400 MHz; (CD$_3$)$_2$SO] 1.80 (4H, m, CH$_2$-2 and 3), 2.55 (2H, t, J=6.0, CH$_2$-1), 2.81 (2H, t, J=5.9, CH$_2$-4), 6.28 (2H, s, NH$_2$), 7.37 (1H, td, J=8.8, 2.8, Ar—H-6), 7.74 (1H, dd, J=9.2, 5.8, Ar—H-5), 7.95 (1H, dd, J=11.2, 2.8, Ar—H-8). $\delta$F [377 MHz, (CH$_3$)$_2$SO] 117.87 (ddd. J=11.1, 8,3, 5.8, Ar—F-7).

EXAMPLE 35

9-Amino-7,8-difluoro-2,3-dihydro-1-H-cyclopenta-[1,2-b] quinoline and 9-amino-6,7-difluoro-2,3-dihydro-1H -cyclopenta [1,2-b] quinoline (10) and (8)

Under nitrogen, titanium tetrachloride (2.4 ml, 22 mmol) was added to 2-(3',4'-difluorophenyl) aminocyclopent-1-ene-1-carbonitrile (Example 30) (4.4 g, 20 mmol) and the stirred mixture was heated at 140° C. for 1 hour. After cooling, 10M-sodium hydroxide (40 ml) was added and the mixture heated under reflux for 1 hour. After being allowed to cool, this mixture was filtered and the solid washed with dichloromethane. Any organics in the filtrate were also extracted into dichloromethane. All extracts were combined, dried (Na$_2$SO$_4$), filtered and the solvent evaporated. Kugelrohr distillation (175–225° C., 0.15 mmHg) followed by chromatography on silica with chloroform-ethanol-10M ammonia solution (200:8:1) as the eluant gave two products. Kugelrohr distillation of the first fraction (140° C., 0.07 mmHg) gave a pale yellow powder. A similar distillation of the second fraction (200° C., 0.1 mmHg) gave an off-white powder.

i) m.p. 177–178° C. (10)

(Found: C, 65.3; H, 4.3; N, 12.65. C$_{12}$H$_{10}$F$_2$N$_2$ requires C, 65.45; H, 4.6; N, 12.7%) $\delta_H$ [250 MHz; (CD$_3$)$_2$SO] 2.05 (2H, quin, J=7.5, CH$_2$-2), 2.81 (2H, t, J=7.4, CH$_2$-1), 2.89 (2H, t, J=7.7, CH$_2$-3), 6.31 (2H, s, NH$_2$), 7.49–7.64 (2H, m, Ar—H-5 and 6).

ii) m.p. 263–265° C. (dec). (8)

(Found: C, 65.3; H, 4.5; N, 12.7. C$_{12}$H$_{10}$F$_2$N$_2$ requires C, 65.45; H, 4.6; N, 12.7%) $\delta_H$ [250 MHz; (CD$_3$)$_2$SO] 2.04 (2H, quin, J=7.5, CH$_2$-2), 2.79 (2H, t, J=7.3, CH$_2$-1), 2.87 (2H, t, J=7.7, CH$_2$-3), 6.54 (2H, s, NH$_2$), 7.59 (1H, dd, J=12.5, 8.2, Ar—H-8), 8.18 (1H, dd, J=12.9, 8.9, Ar—H-5).

EXAMPLE 36

1-(4'Fluorophenyl) amino-2-cyano-3,4-dihydro-naphthalene (Intermediate leading to (27))

4-Fluoro-aniline (Aldrich Chemicals) (1.11 g, 10 mmol) and 2-cyano-3 ,4-dihydro-1 (2H) -naphthalenone (synthesised according to the method of Johnson. W. S. and Shelberg W. E. J. Amer. Chem. Soc., (1945), 67 p.1745.) (91.71 g 10 mmol) were heated together at 150° C. for 1 hour. After cooling, chromatography on silica with chloroform as the eluent followed by Kugelrohr distillation (175° C., 0.2 mmHg) gave the product as pale brown crystals.

m.p. 151–153° C. (Found: C, 77.0; H, 5.0; N, 10.8. C$_{17}$H$_{13}$FN$_2$ requires C, 77.3; H, 5.0; N, 10.6%). $\delta$H (250 MHz; CDCl$_3$) 2.51 (2H, t, J=7.4, CH$_2$-3), 2.90 (2H, t, J=7.4, CH$_2$-4), 6.33 (1H, br s, NH), 6.75 (2H, ABX, J=8.9, 4.6, Ar—H-2' and 6'), 6.91 (2H, ABX, J=8.6, 8.6, Ar—H-3e and 5'), 7.08 (1H, dd, J=7.0, 5.9, 2.3 Ar—H-7), 7.19 (1H, d, J=7.7, Ar—H-5), 7.26 (1H, d, J=6.7, Ar—H-8), 7.27 (1H, td, J=6.9, 1.3, Ar—H-5), 7.26 (1H, d, J=6.7, Ar—H-8), 7.27 (1H, td, J=6.9, 1.3, Ar—H-6).

EXAMPLE 37

7-Amino-9-fluoro-5,6-dihydrobenz[c] acridine (27)

Under nitrogen, titanium tetrachloride (0.3 ml, 2.7 mmol) was added to the above enamine (Example 36) (0.65 g, 2.5 mmol) and the stirred mixture was heated at 140° C. for 1 hour. After cooling, 10M-sodium hydroxide (20 ml) was added and the mixture heated under reflux for 1 hour After being allowed to cool, this mixture was filtered and the solid washed with dichloromethane. Any organics in the filtrate were also extracted into dichloromethane. All extractions were combined, dried (Na$_2$SO$_4$), filtered and the solvent evaporated. Kugelrohr distillation (210° C., 0.07 mmHg) gave the product as a pale yellow powder.

m.p. 158–159° C. (Found: C, 77.0; H, 5.0; N, 10.8. C$_{17}$H$_{13}$FN$_2$ requires C, 77.3; H, 5.0; N, 10.6%). $\delta$H[250 MHz; (CD$_3$)$_2$SO] 2.86 (4H, s, CH$_2$-3 and 4), 6.57 (2H, s, NH$_2$), 7.25–7.37 (3H, m, Ar—H-5, 6 and 7), 7.46 (1H, td, J=8.7, 2.7, Ar—H-11), 7.85 (1H, dd, J=9.2, 3.4, Ar—H-10), 8.03 (1H, dd, J=11.1, 2.8, Ar—H-13), 8.35 (1H, dd, J=7.3, 5.4, Ar—H-8).

EXAMPLE 38

2-(3', 5'-Difluorophenylamino)-cyclopent-1-ene-1-carbonitrile (Intermediate leading to (9))

3,5-Difluoro-aniline (Aldrich Chemicals) (2.6 g, 20.0 mmol), 2-oxocyclopentane carbonitrile (Example 11) (2.2 g, 20.2 mmol), calcium chloride (2.5 g, 22.5 mmol) and T.H.F. were heated under reflux for 24 hours. After cooling the mixture was filtered and the solvent evaporated. Kugelrohr distillation (140° C., 0.3 mmHg) gave the product as pale yellow crystals.

m.p. 113–115° C. (Found: C, 65.2; H, 4.3; N, 12.5. $C_{12}H_{10}F_2N_2$ requires C, 65.45; H, 4.6; N, 12.7%). δH(250 MHz; $CDCl_3$) 2.02 (2H, quin, J=7.4, $CH_2$-4), 2.60 (2H, tt, J=7.6, 1.5, $CH_2$-5), 2.77 (2H, t, J=7.5, $CH_2$-3), 6.50 (1H, tt, J=9.0, 2.2, Ar—$H$-4'), 6.53 (2H, dd, J=10.3, 1.4, Ar—$H$-2' and 6'), 7.01 (1H, br s, N$H$). δF (377 MHz; $CDCl_3$)-108.997 (t, J=8.8, Ar—$F$-3' and 5').

EXAMPLE 39

9-Amino-6,8-difluoro-2.3-dihydro-1H -cyclopenta [1,2-b] quinoline (9)

Under nitrogen, titanium tetrachloride (1.2 ml; 2.1 g; 11.0 mmol) was added to the above enamine (Example 38) (2.2 g, 10.0 mmol) and the stirred mixture was heated at 140° C. for 1 hour. After cooling, sodium hydroxide (10M, 20 ml) was added and the mixture heated under reflux for 1 hour. After being allowed to cool, this was filtered and the solids were washed with dichloromethane. Any organics in the filtrate were also extracted into dichloromethane, the extracts were combined, dried ($Na_2SO_4$), filtered and the solvent evaporated. Kugelrohr distillation (180° C., 0.02 mmHg) gave the product as a very pale yellow powder.

(Found: C, 65.25; H, 4.25; N, 12.65. $C_{12}H_{10}F_2N_2$ requires C, 65.45; H, 4.6; N, 12.7%. vmax 3515, 3311 ($NH_2$). δH[250 MHz; $(CD_3)_2SO$] 2.04 (2H, quin, J=7.5, $CH_2$-2), 2.78 (2H, t, J=7.3, $CH_2$-1), 2.88 (2H, t, J=7.7, $CH_2$-3), 6.38 (2H, br s, $NH_2$), 7.14 (1H, ddd, J=13.6, 9.2, 2.7; Ar—H-7), 7.22 (1H, ddd, J=10.7, 2.6, 1.3, Ar—H-5). δF [377 MHz; $(CD_3)_2SO$] –109.73 (1F, dd, J=13.3, 8.11, Ar—F-8) 111.65 (1F, dt, J=10.6, 8.6, Ar—F-6).

EXAMPLE 40

2-(2'-Methylphenyl)-aminocyclopent-1-enecarbonitrile 2-methylaniline (Avocado) (2.2 g, 20.6 mmol), 2-oxocyclopentanecarbonitrile (Example 11) (2.2 g, 20.2 mmol), calcium chloride (2.5 g, 22.5 mmol) and T.H.F. (30 ml) were heated under reflux for 16 hours. After cooling, the mixture was filtered and the solvent evaporated. Kugelrohr distillation (130° C., 0.5 mmHg) gave the product as a brown solid.

m.p. 88–92° C. (Found: C, 78.5; H, 7.3; N, 14.0 Calc. for $C_{13}H_{14}N_2$; C, 78.75; H, 7.1; N, 14.1%). δH [250 MHz; $(CD_3)_2CO$] 1.85 (2H, quin, J=6.8, $CH_2$-4), 2.27 (3H, s, C$H_3$), 2.50 (4H, t, J=6.8, $CH_2$-3, $CH$-$_2$-5), 7.05–7.23 (4H, m, Ph—H), 7.55 (1H, s, N$H$), vmax (KBr)/$cm^{-1}$ 13285 (N—H), 3030 (Ar—H), 2928, 2877 (C—H), 2187 (CN), 1626 (Ar).

EXAMPLE 41

9-Amino-5-methyl-2.3-dihydro-1H -cyclopenta[1,2-b] quinoline (21)

2-(2'-methylphenyl)-aminocyclopent-1-ene-carbonitrile (Example 40) (2.0 g, 10.1 mmol) and titanium tetrachloride (1.2 ml, 11.0 mmol) were heated together at 140° C. for 1 hour, under nitrogen. After cooling, 10M-sodium hydroxide (20 ml) was added. The mixture was heated under reflux for 1 hour. The product was extracted into dichloromethane, dried ($Na_2SO_4$) filtered and the solvent evaporated. Kugelrohr distillation (195° C., 0.15 mmHg) gave the product as yellow crystals.

m.p. 198–200° C. (Found: C, 79.0; H, 7.0; N, 14.0. $C_{13}H_{14}N_2$ requires that C, 78.75; H, 7.1; N, 14.1%). δH[250 MHz; $(CD_3)_2SO$] 2.05 (2H, quin, J=7.4, $CH_2$-2), 2.58 (3H, s, C$H_3$), 2.81 (2H, t, J=7.3, $CH_2$-1), 2.91 (2H, t, J=7.6, C$H_2$-3), 6.33 (2H, s, N$H_2$), 7.17 (1H, t, J=7.6, Ar—$H$-7), 7.35 (1H, d, J=6.5, Ar—$H$-6), 7.95 (1H, d, J=8.3, Ar—$H$-8), vmax (KBr)/$cm^{-1}$ 3489 (N—H). 3183 (Ar—H), 2953 (c—H), 1677 (Ar).

EXAMPLE 42

2-(4-Methylphenyl)-aminocyclopent-1-ene-carbonitrile

4-Methylaniline (Aldrich Chemicals) (92.2 g, 20.6 mmol), 2-oxocyclopentanecarbonitrile (Example 11) (2.2 g, 20.2 mmol), calcium chloride (2.5 g, 22.5 mmol) and T.H.F. (30 ml) were heated under reflux for 16 hours. After cooling, the mixture was filtered and the solvent evaporated. Kugelrohr distillation (125° C., 0.06 mmHg) gave the product as a brown solid.

m.p. 110–112° C. (Found: C, 77.7; H, 7.3; N, 13.7 Calc. for $C_{13}H_{14}N_2$ C, 78.75; H, 7.1; N, 14.1%). $\delta_H$ [250 MHz; $(CD_3)_2SO$] 1.91 (2H, quin, J=7.4, $CH_2$-4), 2.27 (3H, s, C$H_3$), 2.52 (2H, t, J=5.7, $CH_2$-3), 2.65 (2H, t, J=7.1, $CH_2$-5), 7.04–7.14 (4H, m, Ph—$H$), 7.95 (1H, s, N$H$), vmax (KBr)/$cm^{-1}$ 3311 (N—H), 3106, 3030 (Ar—H), 2279, 2877 (C—H), 2187 (CN), 1651 (Ar).

EXAMPLE 43

9-Amino-7-methyl-2,3-dihydro-1H-cyclopenta [1,2-b] quinoline (24)

2-(4'-Methylphenyl)-aminocyclopent-1-ene-carbonitrile (Example 42) (2.0 g, 10.1 mmol) and titanium tetrachloride (1.2 ml, 11.0 mmol) were heated together at 140° C. for 1 hour, under nitrogen. After cooling, 10M-sodium hydroxide (20 ml) was added. The mixture was heated under reflux for 1 hour. The product was extracted into dichloromethane, dried ($Na_2SO_4$), filtered and the solvent evaporated. Kugelrohr distillation (180° C., 0.1 mmHg) gave the product as yellow crystals.

m.p. 200–202° C. (Found: C, 78.8; H. 7.2; N. 13.9 $C_{13}H_{14}N_2$ requires that C, 78.75; H, 7.1; N, 14.1%). δH [250 MHz; $(CD_3)_2SO$] 2.03 (2H, quin, J=7.5, $CH_2$-2), 2.43 (3H, s, C$H_3$), 2.79 (2H, t, J=7.4, $CH_2$-1), 2.86 (2H, t, J=7.6, C$H_2$-3), 6.29 (2H, s, N$H_2$), 7.32 (1H, dd, J=8.5 and 1.5, Ar—H-6), 7.56 (1H, d, J=8.5, Ar—$H$-5), 7.90 (1H, s, Ar—$H$-8). vmax (KBr)/$cm^{-1}$ 3489, 3438 (N—H), 3157 (Ar—H), 2928, 2851 (C—H), 1677 (Ar).

EXAMPLE 44

2-(2',5'-Dimethylphenyl)-aminocyclopent-1-ene-carbonitrile 2,5-Dimethylaniline (Avocado) (2.4 g, 19.8 mmol), 2-oxocyclopentanecarbonitrile (Example 11) (2.2 g, 20.2 mmol), calcium chloride (2.5 g, 22.5 mmol) and T.H.F. (30 ml) were added under reflux for 17 hours. After cooling, the mixture was filtered and the solvent evaporated. Kugelrohr distillation (125° C., 0.08 mmHg) gave a brown oil which slowly crystallised over time.

m.p. 105–107° C. (Found: C, 78.6; H, 7.5; N, 12.8 $C_{14}H_{16}N_2$ requires that C, 79.2; H, 7.6; N, 13.2%). δH [250

MHz; (CD$_3$)$_2$CO] 1.89 (2H, quin, J=7.4, C$\underline{H}_2$-4), 2.22 (3H, s, C$\underline{H}_3$), 2.27 (3H, s, C$\underline{H}_3$), 2.53 (4H, m, C$\underline{H}_2$-5, C$\underline{H}_2$-3), 6.92 (1H, d, J=7.5, Ar—$\underline{H}$-4), 6.98 (1H , s, Ar—$\underline{H}$-6), 7.08 (1H, d, J=7.8, Ar—H-3), 7.51 (1H , s, N$\underline{H}$). vmax (KBr)/cm$^{-1}$ 3285 (N—H), 3055 (Ar—H), 2979, 2928 (C—H), 2187 (CN), 1651 (AR).

EXAMPLE 45

9-Amino-5,8-dimethyl-2,3-dihydro-1H -cyclopenta [1,2-b] quinoline (20)

2-(2',5'-Dimethylphenyl)-aminocyclopent-1-ene-carbonitrile (Example 44) (2.1 g, 9.7 mmol) and titanium tetrachloride (1.2 ml, 11.0 mmol) were heated together at 140° C. for 1 hour, under nitrogen. After cooling, 10M-sodium hydroxide (20 ml) was added. The mixture was heated under reflux for 1 hour. The product was extracted into dichloromethane, dried (Na$_2$SO$_4$), filtered and the solvent evaporated. Kugelrohr distillation (160° C., 0.15 mmHg) gave the product as a yellow oil which slowly crystallised over time.

m.p. 95–97° C. (Found: C, 74.9; H, 8.0; N, 12.6 C$_{14}$H$_{11}$N$_2$ requires that C, 79.2; H, 7.6; N, 13.2%). δH [250 MHz; CDCl$_3$] 2.19 (2H, quin, J=7.6, C$\underline{H}_2$-2), 2.67 (3H, s, C$\underline{H}_3$), 2.80 (2H, t, J=6.8, C$\underline{H}_2$-1), 2.91 (3H, s, C$\underline{H}_3$) , 3.11 (2H, t, J=7.5, C$\underline{H}$-3), 4.73 (2H, s, N$\underline{H}_2$), 6.95 (1H , d, J=5.0, Ph—H), 7.25 (1H, d, J=7.5, Ph—$\underline{H}$). vmax (KBr)/cm$^{-1}$ 3489, 3462 (N—H), 3260 (Ar—H), 2928, 2851 (C—H), 1651 (Ar).

EXAMPLE 46

2-(2',4'-Dimethylphenyl)-aminocyclopent-1-ene-carbonitrile 2,4-Dimethylaniline (Fluka) (2.4 g, 19.8 mmol), 2-oxocyclopentanecarbonitrile (Example 11) (2.2 g, 20.2 mmol), calcium chloride (2.5 g, 22.5 mmol) and T.H.F. (30 ml) were heated under reflux for 17 hours. After cooling, the mixture was filtered and the solvent evaporated. Kugelrohr distillation (150° C., 0.1 mmHg) gave the product as a brown solid.

m.p. 113–116° C. (Found: C, 78.8; H, 7.9; N, 12.7 C$_{14}$H$_{16}$N$_2$ requires that C, 79.2; H, 7.6; N, 13.2%). δH [250 MHz; (CD$_3$)$_2$CO] 1.88 (2H, quin, J=7.4, C$\underline{H}_2$-4), 2.24 (3H, s, C$\underline{H}_3$), 2.27 (3H, s, C$\underline{H}_3$), 2.51 (4H, m, C$\underline{H}_2$-5, C$\underline{H}_2$-3), 6.95–7.05 (3H, m, Ph—$\underline{H}$), 7.46 (1H , s, N$\underline{H}$). vmax (KBr)/cm$^{-1}$ 3259 (N—H), 3055 (Ar—$\underline{H}$), 2979, 2928 (C—H), 2187 (CN), 1626 (Ar).

EXAMPLE 47

9-Amino-5-7-Dimethyl-2,3-dihydro-1H-cyclopenta [1,2-b] quinoline (23)

2-(2',4'-Dimethylphenyl)-aminocyclopent-1-ene-carbonitrile (Example 46) (2.0 g, 9.4 mmol) and titanium tetrachloride (1.2 ml, 11.0 mmol) were heated together at 140° C. for 1 hour, under nitrogen. After cooling, 10M-sodium hydroxide (20 ml) was added. The mixture was heated under reflux for 1 hour. The product was extracted into dichloromethane, dried (Na$_2$SO$_4$), filtered and the solvent evaporated. Kugelrohr distillation (160° C,, 0.01 mmHg) gave the product as a pale yellow solid.

m.p. 211–213° C. (Found: C, 79.1; H, 7.4; N, 12.9 C$_{14}$H$_{16}$N$_2$ requires that C, 79.2; H, 7.6; N, 13.2%). δH [250 MHz; (CD$_3$)$_2$SO] 2.03 (2H, quin, J=7.5, C$\underline{H}_2$-2), 2.39 (3H, s, C$\underline{H}_3$), 2.54 (3H, s, C$\underline{H}_3$), 2.79 (2H, t, J=7.3, C$\underline{H}_2$-1), 2.88 (2H, t, J=7.6, C$\underline{H}_2$-3), 6.22 (2H, s, N$\underline{H}_2$), 7.20(1H , s, Ph—$\underline{H}$), 7.73 (1H , s, Ph—$\underline{H}$). vmax (KBr)/cm$^{-1}$ 3489, 3438 (N—H), 3209 (Ar—H), 2979, 2928, (C—H) 1651 (Ar)

EXAMPLE 48

2-(2',3'-Dimethylphenyl)-aminocyclopent-1-ene-carbonitrile 2,3-Dimethylaniline (Aldrich) (2.4 g, 19.8 mmol), 2-oxocyclopentanecarbonitrile (Example 11) (2.2 g, 20.2 mmol), calcium chloride (2.5 g, 22.5 mmol) and T.H.F. (30 ml) were heated under reflux for 17 hours. After cooling, the mixture was filtered and the solvent evaporated. Kugelrohr distillation (140° C., 0.06 mmHg) gave the product as a yellow solid.

m.p. 100–103° C. (Found: C, 79.0; H, 7.9; N, 13.1 C$_{14}$H$_{16}$N$_2$ requires C, 79.2; H, 7.6; N, 13.2%). δH [250 MHz; (CDCl$_3$] 1.92 (2H, quin, J=7.3, C$\underline{H}_2$-4), 2.19 (3H, s, C$\underline{H}_3$), 2.31 (3H, s, C$\underline{H}_3$), 2.46 (2H, t, J=7.5, C$\underline{H}_2$-3), 2.60 (2H, t, J=7.1, C$\underline{H}_2$-5), 6.17 (2H, s, N$\underline{H}_2$), 6.93–7.17 (3H, m, Ph—$\underline{H}$). vmax (KBr)/cm$^{-1}$ 3311 (N—H), 3080 (Ar—H), 2928, 2877 (C—H), 2187 (CN), 1651 (Ar)

EXAMPLE 49

9-Amino-5,6-dimethyl-2,3-dihydro-1H-cyclopenta [1,2-b] quinoline (26)

2-(2',3'-Dimethylphenyl)-aminocyclopent-1-ene-carbonitrile (Example 48) (1.2 g, 5.8 mmol) and titanium tetrachloride (0.7 ml, 5.8 mmol) were heated together at 140° C. for 1 hour, under nitrogen. After cooling, 10M-sodium hydroxide (20 ml) was added. The mixture was heated under reflux for 1 hour. The product was extracted into dichloromethane, dried (Na$_2$SO$_4$), filtered and the solvent evaporated. Kugelrohr distillation (160° C., 0.06 mmHg) gave the product as yellow crystals.

m.p. 215–216° C. (Found: C, 79.3; H, 8.0; N, 11.9 C$_{14}$H$_{16}$N$_2$ requires C, 79.2; 7.6; N, 13.2%). δH [250 MHz; (CD$_3$)$_2$SO] 2.04 (2H, quin, J=7.6, CH$_2$-2), 2.37 (3H, s, C$\underline{H}_3$), 2.54 (3H, s, C$\underline{H}_3$), 2.79 (2H, t, J=7.3, C$\underline{H}_2$-1), 2.90 (2H, t, J=7.8, C$\underline{H}_2$-3), 6.26 (2H, s, N$\underline{H}_2$), 7.11 (1H , d, J=8.5, Ph—$\underline{H}$), 7.85 (1H , d, J=8.5, Ph—$\underline{H}$). vmax (KBr)/cm$^{-1}$ 3489, 3438 (N—H), 3183 (Ar—H), 2928 (C—H), 1651 (Ar).

EXAMPLE 50

2-(3',5'-Dimethylphenyl)-aminocyclopent-1-ene-carbonitrile 3,5-Dimethylaniline (Aldrich Chemicals) (2.4 g, 19.8 mmol), 2-oxocyclopentanecarbonitrile (Example 11) (2.2 g, 20.2 mmol), calcium chloride (2.5 g, 22.5 mmol) and T.H.F. (30 ml) were heated under reflux for 18 hours. After cooling, the mixture was filtered and the solvent evaporated. Kugelrohr distillation (150° C., 0.3 mmHg) gave the product as a yellow solid.

m.p. 150–151° C. (Found: C, 79.2; H, 7.6; N, 13.2 C$_{14}$H$_{16}$N$_2$ requires that C, 79.2; H, 7.6; N, 13.2%). δH [250 MHz; (CD$_3$)$_2$SO] 1.92 (2H, quin, J=7.3, C$\underline{H}_2$-4), 2.25 (6H, s, C$\underline{H}_3$), 2.53 (2H, td, J=8.5 and 1.3, C$\underline{H}_2$-3), 2.68 (2H, t, J=7.5, C$\underline{H}_2$-5), 6.70 (1H , s, Ar—$\underline{H}$-4), 6.78 (2H, s, Ar—$\underline{H}$-2, Ar—$\underline{H}$-6), 7.90 (1H, s, NH). vmax (KBr)/cm$^{-1}$ 3285 (N—H), 3030(Ar—H), 2928, 2877 (C—H), 2187 (CN), 1651 (Ar).

EXAMPLE 51

9-Amino-6,8-dimethyl-2,3-Dihydro-1H -cyclopenta [1,2-b] quinoline (30)

2-(3',5'-Dimethylphenyl) aminocyclopent-1-ene-carbonitrile (Example 50) (1.5 g, 7.1 mmol) and titanium tetrachloride (1.2 ml, 11.0 mmol) were heated together at 140° C. for 1 hour, under nitrogen. After cooling, 10M-sodium hydroxide (20 ml) was added. The mixture was heated under reflux for 1 hour. The product was extracted into dichloromethane, dried ($Na_2SO_4$), filtered and the solvent evaporated. Kugelrohr distillation (180° C., 0.3 mmHg) gave the product as a white solid.

m.p. 132–135° C. δH [250 MHz; $(CD_3)_2SO$] 2.03 (2H, quin, J=7.6, C$\underline{H}_2$-2), 2.32 (3H, s, C$\underline{H}_3$), 2.77 (2H, t, J=7.5, C$\underline{H}_2$-1), 2.85 (2H, t, J=7.9, $CH_2$-3), 2.84 (3H, s, $CH_3$), 5.74 (2H, s, N$\underline{H}_2$), 6.86 (1H , s, Ph—$\underline{H}$), 7.29 (1H , s, Ph—$\underline{H}$). vmax (KBr)/$cm^{-1}$ 3489, 3438 (N—H), 3030 (Ar—H), 2953, 2877 (C—H), 1651 (Ar).

EXAMPLE 52

9-Amino-2,3-dihydro-[1H ]-cyclopenta-[b]-quinoline (29)

Anthranilonitrile (5.0 g, 42.3 mmol), cyclopentanone (4.1 g, 46.7 mmol), boron trifluoride diethyl etherate (1M, 10 ml, 81.8mmol) were treated according to the general procedure to give the title compound.

Recrystallised: m.p. 180–182° C. (aq. EtOH) (lit. 183–183.5° C.)$^R$. Found: C, 78.15; H, 6.5; N, 14.95. Calculated for $C_{12}H_{12}N_2$: C, 78.35; H, 6.55; N, 15.2%. δH (250 MHz, $CDCl_3$) 2.19 (2H, quintet, J=7.6, $CH_2$), 2.88 (2H, t, J=7.5, $CH_2$), 3.10 (2H, t, J=7.8, $CH_2$), 4.65 (2H br s, exchanges with $D_2O$, $NH_2$), 7.33 (1H, t, J=8.05, aryl-H) , 7.57 (1H, t, J=8.11, aryl-H), 7.71 (1H, d, J=8.3, aryl-H), 7.89 (1H , d, J=8.4, aryl-H).
Maleate salt m.p. 100–105° C. Found: C, 63.9; H, 5.3; N, 9.3. Calculated for $C_{12}H_{12}N_2.C_4H_4O_4$: C, 64.0; H, 5.4; N, 9.3%. δH(250 MHz, $CD_3OD$) 2.34 (2H, quintet, J=7.8, $CH_2$), 2.97 (2H, t, J=7.1, $CH_2$), 3.23 (2H, t, J=7.8, $CH_2$), 6.23 (2H, s, maleate), 7.61 (1H, td, J=6.9, 1.3, aryl-H), 7.35 (1H, d, J=8.5, aryl-H), 7.86 (1H, td, J=6.9, 1.2, aryl-H), 8.23 (1H; dd, J=8.5, 0.7, aryl-H).

EXAMPLE 53

9-Amino-5-hydroxy-2,3-dihydro-1H-cyclopenta [b] quinoline (12)

Under nitrogen, titanium tetrachloride (3.46 g, 18.2 mmol) was added to 2-(2'-methoxyphenyl) aminocyclopent-1-ene (3.4 g, 15.9 mmol) and the stirred mixture was heated at 140° C. for 1 hour. After cooling, 10M-sodium hydroxy solution (20 $cm^3$) was added and the mixture heated under reflux for 1 hour. After being allowed to cool, the mixture was filtered and the solids washed with dichloromethane. Any organics in the filtrate were also soxhlet extracted into dichloromethane. All extracts were combined, dried ($Na_2SO_4$), filtered and the solvent evaporated. Purification by recrystallisation (ethanol) and Kugelrohr distillation gave the title compound as an off-white powder.

m.p. 187–188° C. Found: C, 71.75; H, 6.08; N, 13.73%. $C_{12}H_{12}N_2O$ requires: C, 71.98; H, 6.04; N, 13.99%. vmax (KBr)/$cm^{-1}$ 3566, 3438 (N—H str), 3438 (OH str), 2928 (C—H str), 1651–1498 (C=C str). $δ_H$ [250 MHz; $(CD_3)_2$ SO] 2.07 (2H, quin, J=7.5, $CH_2$-2), 2.81 (2H, t, J=7.3, $CH_2$-1), 2.94 (2H, t, J=7.6, $CH_2$-3), 4.36 (1H , br s, OH), 6.47 (2H, s, $NH_2$), 6.86 (1H , d, J=7.4, Ar—H-6), 7.13 (1H, t, J=7.9, Ar—H-7), 7.54 (1H , d, J=8.3, Ar—H-8). m/z 200.0953 ($M^+$, 100%), 199.0878 ($M^+$—H, 30%) [theory m/z 200.0949, 199.0871].

EXAMPLE 54

Pharmacology

Four assays were employed to measure biological activity:
Inhibition of Acetylcholinesterase uptake activity (AChE)
Inhibition of Butyrylcholinesterase activity (BChE)
Inhibition of 5-HT (serotonin) uptake
Inhibition of noradrenaline uptake (NA).

The details of the assays employed are the same as for those outlined in Examples 8(A) to 8(C) inclusive, except that the drugs tested and results are as shown in Tables 2 and 3.

As in Example 8, the biological activity of primary interest was that of AChE and 5-HT uptake. BChE uptake was measured such that compounds selective for AChE could be located. Inhibition of noradrenaline uptake was measured since compounds having the ability to potentiate transmission involving noradrenaline as well as 5-HT and acetylcholine are of interest.

TABLE 2

| COMPOUND | AChE IC50 #μM | TACRINE RATIO | BChE IC50 #μM | TACRINE RATIO |
|---|---|---|---|---|
| TACRINE | 0.078 | 1.000 | 0.025 | 1.00 |
| 8 | 0.035 | 2.229 | 10.000 | 0.003 |
| 9 | 0.120 | 0.650 | 1.400 | 0.018 |
| 10 | 0.410 | 0.190 | 15.000 | 0.002 |
| 11 | 0.120 | 0.650 | 0.750 | 0.033 |
| 12 | 1.000 | 0.078 | 0.500 | 0.050 |
| 13 | 0.290 | 0.269 | 0.270 | 0.093 |
| 14 | 0.078 | 1.000 | 1.510 | 0.017 |
| 15 | 0.064 | 1.219 | 0.041 | 0.610 |
| 16 | 0.140 | 0.557 | 0.530 | 0.047 |
| 17 | 0.010 | 8.041 | 0.13 | 0.19 |
| 18 | 0.200 | 0.390 | 0.410 | 0.061 |
| 19 | 1.300 | 0.060 | 1.32 | 0.019 |
| 20 | 1.900 | 0.041 | 1.400 | 0.018 |
| 21 | 3.300 | 0.024 | 13.800 | 0.002 |
| 22 | 3.500 | 0.022 | 14.500 | 0.002 |
| 23 | 19.000 | 0.004 | 52.000 | 0.000 |
| 24 | 6.700 | 0.012 | 1.100 | 0.023 |
| 25 | 10.000 | 0.008 | 1.900 | 0.013 |
| 26 | 11.600 | 0.007 | 9.200 | 0.003 |
| 27 | 18.000 | 0.004 | NB | XXXXX |
| 28 | 39.600 | 0.002 | 13.800 | 0.002 |
| 29 | 0.056 | 1.393 | 0.052 | 0.481 |
| 30 | 0.130 | 0.600 | 0.710 | 0.035 |
| 31 | 0.470 | 0.166 | 4.800 | 0.005 |
| 32 | 0.540 | 0.144 | 8.800 | 0.003 |
| 33 | 36 | 0.002 | N/A | N/A |
| 34 | 2.900 | 0.030 | N/A | N/A |
| 35 | >100 | N/A | N/A | N/A |
| 36 | 47.000 | 0.002 | N/A | N/A |

NA = NOT ATTEMPTED
NB = No Block at 100 μM.

TABLE 3

| COMPOUND | 5-HT UPTAKE INHIBITION #μM | TACRINE RATIO | NA UPTAKE INHIBITION #μM | TACRINE RATIO |
|---|---|---|---|---|
| TACRINE | 7.600 | 1.000 | 6.700 | 1.000 |
| 8 | 2.000 | 3.800 | NA | NA |
| 9 | 52.000 | 0.146 | NA | NA |
| 10 | 260.000 | 0.029 | NA | NA |
| 11 | 3.700 | 2.054 | 12.000 | 0.558 |
| 12 | 14.500 | 0.524 | 0.700 | 9.571 |
| 13 | 42.000 | 0.181 | 0.700 | 9.571 |
| 14 | 43.000 | 0.177 | 3.300 | 2.030 |
| 15 | 22.000 | 0.345 | 0.700 | 9.571 |

TABLE 3-continued

| COMPOUND | 5-HT UPTAKE INHIBITION #μM | TACRINE RATIO | NA UPTAKE INHIBITION #μM | TACRINE RATIO |
|---|---|---|---|---|
| 16 | 39.000 | 0.195 | 0.002 | 3350.000 |
| 17 | 1.500 | 5.067 | NA | NA |
| 18 | 2.300 | 3.304 | NA | NA |
| 19 | 7.000 | 1.086 | 2.700 | 2.481 |
| 20 | 3.900 | 1.949 | NA | NA |
| 21 | 12.000 | 0.633 | NA | NA |
| 22 | 104.000 | 0.073 | 3.100 | 2.161 |
| 23 | 7.900 | 0.962 | NA | NA |
| 24 | 17.000 | 0.447 | NA | NA |
| 25 | 5.300 | 1.434 | NA | NA |
| 26 | 4.400 | 1.727 | NA | NA |
| 27 | 3.500 | 2.171 | NA | NA |
| 28 | 5.800 | 1.310 | NA | NA |
| 29 | 21.000 | 0.362 | 0.600 | 11.167 |
| 30 | 8.100 | 0.938 | NA | NA |
| 33 | 18.000 | 0.400 | NA | NA |
| 34 | 18.000 | 0.400 | NA | NA |
| 35 | 114.000 | 0.070 | NA | NA |
| 36 | 29.000 | 0.300 | NA | NA |

NA = Not attempted
NB = No block at 100 μM

What is claimed is:

1. The compound:

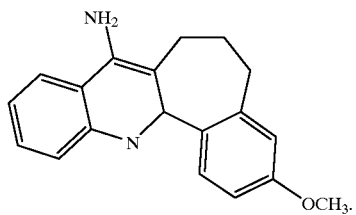

2. The compound:

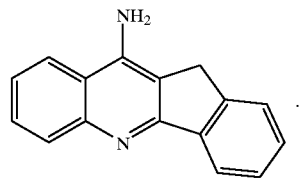

3. A process for preparing a compound according to Formula (11(c)):

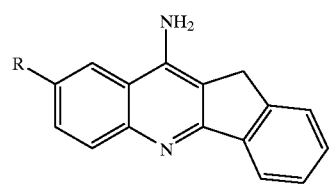

(II(c))

wherein

R is selected from H, F, Cl, Br and OCH$_3$; by
(i) condensing a 1-indanone with an alkyl formate forming a 2-OH methylene indan-1-one;
(ii) condensing the 2-OH-methylene indan-1-one with a phenyl hydrazine of Formula (VIII):

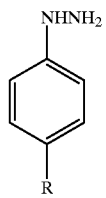

(VIII)

wherein
R is selected from H, F, Cl, Br, and OCH$_3$;
forming an indenopyrazole of Formula (IX):

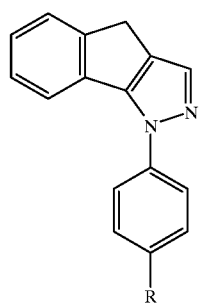

(IX)

(iii) opening the pyrazole ring and forming a phenyl amino cyano-1-indene of Formula (X):

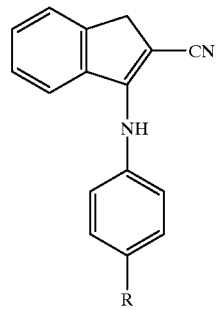

(X)

followed by Lewis base catalysis.

4. A process for preparing a compound of Formula (III) comprising
(i) condensing a cyclic a-cyanoketone of Formula (XI)

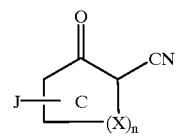

(XI)

wherein
X represents —(CH$_2$)— and n is a whole integer selected from 1 and 2; and
J is a 6 carbon-membered unsubstituted ring optionally fused to Ring C at any face of Ring C with the proviso that the said 6 carbon-membered unsubstituted ring is fused at a face which does not extend from the cyano or ketone substituted carbon of Ring C;

with an aniline derivative of Formula (XII):

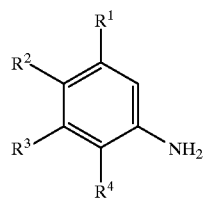

(XII)

wherein
R¹ is selected from H, $NH_2$, OH, F, Cl, Br, I, $OCH_3$, $C_1-C_6$ alkyl and aryl (phenyl);
R² is selected from H, $C_1-C_6$ alkyl, $C_1-C_6$ alkoxy, Cl, Br, F, I and OH;
R³ is selected from H, F, Cl, Br, I, OH, $OCH_3$, and $C_1-C_6$ alkyl;
R⁴ is selected from H, F, Cl, Br, I, $OCH_3$, OH, and $C_1-C_6$ alkyl; and
(ii) cyclising the condensation product of step (i) using a Lewis acid.

5. A process according to claim 4 wherein the α cyanoketone of Formula (XI) is

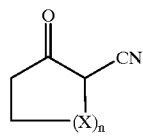

(XI)

wherein X represents —($CH_2$)— and n is a whole integer selected from 1 and 2; and the aniline derivative of Formula (XII) is

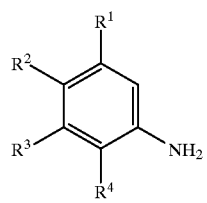

(XII)

wherein R¹, R², R³ and R⁴ are independently selected from H, Br, Cl, OH, $CH_3$ and $OCH_3$.

6. A process according to claim 4 wherein R¹, R², R³ and R⁴ of the aniline derivative of Formula (XII) are independently selected from H, F, Cl and OH.

7. A method for the treatment of Alzheimer's disease in a patient which comprises administering to the patient a clinically useful amount of at least a compound of Formula 11(c)

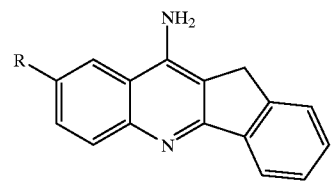

(II(c))

wherein R is selected from H, F, Cl, Br and $OCH_3$, or a pharmaceutically acceptable salt thereof.

8. A method according to claim 7 wherein the compound is administered in association with a pharmaceutically acceptable carrier.

9. A method for the treatment of Alzheimer's disease in a patient which comprises administering to the patient a clinically useful amount of at least a compound of Formula (II (d)):

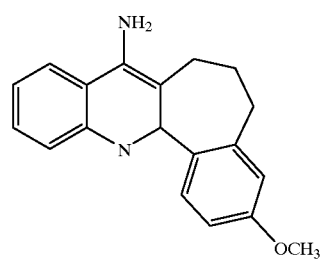

(II(d))

or a pharmaceutically acceptable salt thereof, together with a pharmaceutically acceptable carrier.

10. A pharmaceutical formulation comprising a compound of Formula (II (d)):

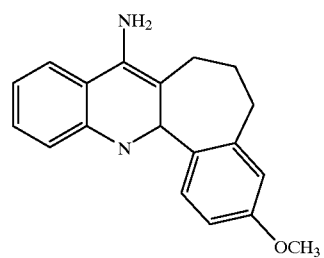

(II(d))

or a pharmaceutically acceptable salt thereof, together with a pharmaceutically acceptable carrier.

* * * * *

UNITED STATES PATENT AND TRADEMARK OFFICE
CERTIFICATE OF CORRECTION

PATENT NO. : 6,130,228
DATED : October 10, 2000
INVENTOR(S) : Proctor et al.

It is certified that error appears in the above-identified patent and that said Letters Patent is hereby corrected as shown below:

Title page, [56] References Cited:
U.S. PATENT DOCUMENTS, "Sigale, Jr. et al." should read --Sigal, Jr. et al.--.
OTHER PUBLICATIONS, line 26, "112191u" should read --112192u--.

Column 48, line 50, "a-cyanoketone" should read --α-cyanoketone--.

Column 50, line 2 "11(c)" should read --II(c)--.

Signed and Sealed this

Eighth Day of May, 2001

Attest:

NICHOLAS P. GODICI

*Attesting Officer*  *Acting Director of the United States Patent and Trademark Office*